United States Patent
Hölscher et al.

(10) Patent No.: US 9,340,751 B2
(45) Date of Patent: May 17, 2016

(54) USE OF SPECIFIC COMPOUNDS FOR MODIFYING ODORS

(71) Applicant: Symrise AG, Holzminden (DE)

(72) Inventors: Bernd Hölscher, Halle (DE); Annabel Chmelnyk, Holzminden (DE)

(73) Assignee: Symrise AG, Holzminden (DE)

( * ) Notice: Subject to any disclaimer, the term of this patent is extended or adjusted under 35 U.S.C. 154(b) by 114 days.

(21) Appl. No.: 13/886,134

(22) Filed: May 2, 2013

(65) Prior Publication Data

US 2013/0303432 A1 Nov. 14, 2013

Related U.S. Application Data

(60) Provisional application No. 61/645,189, filed on May 10, 2012.

(30) Foreign Application Priority Data

May 10, 2012 (EP) .................................... 12167516

(51) Int. Cl.
| | | |
|---|---|---|
| *C11B 9/00* | (2006.01) | |
| *A61Q 13/00* | (2006.01) | |
| *C11D 3/50* | (2006.01) | |
| *A61K 8/35* | (2006.01) | |
| *A61K 8/49* | (2006.01) | |
| *A61Q 5/02* | (2006.01) | |
| *A61Q 19/10* | (2006.01) | |

(52) U.S. Cl.
CPC ................. *C11B 9/0084* (2013.01); *A61K 8/35* (2013.01); *A61K 8/4973* (2013.01); *A61Q 13/00* (2013.01); *C11B 9/0038* (2013.01); *C11D 3/50* (2013.01); *A61Q 5/02* (2013.01); *A61Q 19/10* (2013.01)

(58) Field of Classification Search
CPC ........................................................ A61Q 13/00
USPC ............................................................. 512/11
See application file for complete search history.

(56) References Cited

U.S. PATENT DOCUMENTS

| | | | |
|---|---|---|---|
| 8,034,761 B2 * | 10/2011 | Widder et al. | .................. 512/11 |
| 2003/0152538 A1 * | 8/2003 | Preti et al. | ........................ 424/65 |
| 2010/0111889 A1 | 5/2010 | Marsh | |

OTHER PUBLICATIONS

Sigma Aldrich Product Information for Dihydromyrcenol obtained Mar. 13, 2015 at http://www.sigmaaldrich.com/catalog/product/aldrich/w516406?lang=en&region=US.*
Sigma Aldrich Product Information for Methyl DihydroJasmonate obtained Mar. 13, 2015 at http://www.sigmaaldrich.com/catalog/product/aldrich/w340804?lang=en&region=US.*

* cited by examiner

*Primary Examiner* — Ling Choi
*Assistant Examiner* — Lanee Reuther
(74) *Attorney, Agent, or Firm* — Dilworth & Barrese, LLP

(57) ABSTRACT

The use of certain compounds for masking or decreasing the or one or a plurality of unpleasant olfactory impressions of one or a plurality of substances with an unpleasant odor and/or for enhancing the or one or a plurality of pleasant olfactory impressions of one or a plurality of substances with a pleasant odor and new fragrance mixtures and perfumed products containing such compounds.

11 Claims, No Drawings

USE OF SPECIFIC COMPOUNDS FOR MODIFYING ODORS

CROSS-REFERENCE TO RELATED APPLICATIONS

This application claims the benefit of U.S. Provisional Application Ser. No. 61/645,189, filed on 10 May 2012, the benefit of the earlier filing date of which is hereby claimed under 35 U.S.C. §119(e). This application claims the benefit of EP patent application Ser. No. 12 167 516.9, filed on 10 May 2012, the benefit of the earlier filing date of which is hereby claimed under 35 U.S.C. §119(a)-(d) and (f). Each application is hereby incorporated in its entirety as if fully set forth herein.

BACKGROUND OF THE INVENTION

1. Field of the Invention

The present invention relates to compounds and methods for masking or decreasing the or one or a plurality of unpleasant olfactory impressions of one or a plurality of substances with an unpleasant odor, and compounds and methods for enhancing one or more pleasant olfactory impressions of one more substances with a pleasant odor.

2. Description of Related Art

Basically the perfume industry has a constant need to intensify (accentuate/enhance) the pleasant olfactory aspects of fragrances and to mask or decrease unpleasant olfactory aspects. Flowery fragrances in particular, that is to say fragrances with a flowery note, play an important role in perfumery. Here it is desired on the one hand to particularly accentuate the natural freshness and/or radiance and on the other to suppress the fatty, metallic and/or technical notes.

The reduction of unpleasant odors is in particular a problem that is difficult to deal with and solve in perfume/composition terms. Above all, the particular nature of an unpleasant odor in each case strictly limits the application possibilities. Frequently a reduction in unpleasant odors can at best be achieved by combining with a specially developed perfume oil, which has its own specific type of scent. Here the unpleasant olfactory impressions are frequently merely covered up using the aromatic odor of a(nother) substance.

Of considerable advantage, therefore, are substances or materials, that are able to decrease the intensity of unpleasant odors or to even completely remove the unpleasant odor without themselves having a notable olfactory-perfuming intensity or without themselves in the concentration to be used for the purposes of odor reduction having a notable olfactory-perfuming intensity. Such (active) substances could advantageously neutralize unpleasant odors, without simply masking the respective unpleasant odor by a particular characteristic odor. Use of such substances has or would have the advantage that for the scenting or perfuming of items, preparations or products with unpleasant odors by way of example perfume oils of any fragrance can be used. In this way the consumer can be offered a significantly broader choice of scent types.

The literature contains numerous proposals for combating unpleasant odors, as for example illustrated in the following. In WO 01/43784 and U.S. Pat. No. 7,157,411 the use of certain esters, in particular isomenthyl esters such as isomenthyl acetate, as odor-neutralizing substances for reducing unpleasant odors of the most varied kinds is described.

Previous (olfactory) substances or (olfactory) substance mixtures, intended for olfactory enhancement of products, frequently provide an unsatisfactory olfactory reduction in unpleasant odors. The methods known in the prior art for reducing unpleasant odors frequently have the disadvantage that the (olfactory) substance or (olfactory) substance mixtures used have to be employed in considerable quantities, which can lead to cost and application problems.

BRIEF SUMMARY OF THE INVENTION

Briefly described, in a preferred form, the present invention comprises the use of an individual compound of formula (I) or a mixture comprising or consisting of two or a plurality of compounds of formula (I) (as described herein)

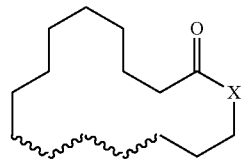

(I)

wherein for the compound of formula (I) or for each compound of formula (I) it is the case that none, one or two of the four jagged lines denotes or denote a double bond and the other jagged lines in each case denote a single bond and X is selected from —O—, —CH2— and —O—CH2—, (a) for masking or decreasing the or one or a plurality of unpleasant olfactory impressions of one or a plurality of substances with an unpleasant odor, wherein the substance(s) is or are not a compound of formula (I), and/or (b) for enhancing the or one or a plurality of pleasant olfactory impressions of one or a plurality of substances with a pleasant odor, wherein the substance(s) is or are not a compound of formula (I).

The invention also concerns new fragrance mixtures, preferably perfume oils, containing or consisting of one or a plurality of such compounds of formula (I) and one or a plurality of specific (further) fragrances (as described herein), wherein the ratio of the total mass of fragrances not corresponding to formula (I) to the total mass of compounds of formula (I) is greater than or equal to 99:1, preferably greater than or equal to 99.9:0.1, particularly preferably greater than or equal to 99.999:0.001.

The present invention further concerns perfumed products, containing a fragrance mixture according to the invention in a sensorially effective quantity, wherein the fragrance mixture as a proportion of the total weight of the product is preferably in the range 0.01 through 10 wt. %, preferably in the range 0.1 through 5 wt. %, particularly preferably in the range 0.25 through 3 wt. %.

The present invention also concerns a method for producing a perfumed product, a method for masking or decreasing the, or one or a plurality of, unpleasant olfactory impressions of one or a plurality of substances with an unpleasant odor and a method for enhancing the or one or a plurality of pleasant olfactory impressions of one or a plurality of substances with a pleasant odor.

Further aspects of the invention arise from the following description, the examples and in particular the attached claims.

The primary object of the present invention was therefore to indicate alternative or improved substances or substance mixtures for reducing, in particular for masking and/or decreasing, unpleasant odors and/or for enhancing pleasant odors.

Here these substances should meet preferably one, a plurality of or preferably all the following requirements:
- be easily accessible,
- be highly effective at low concentrations, preferably with little or no perceptible characteristic odor at low concentrations,
- be extensively or completely colorless,
- be highly stable in various mixtures or preparations, wherein in particular no discoloration and/or Separation and/or clouding should occur,
- behave inertly,
- have no toxic and/or allergic effect on persons.

As regards the term "decreasing", it should be noted that this means a particular form of change in odor, namely a weakening of the intensity of an (unpleasant) odor as opposed to merely overlaying/masking this with a(nother) more dominant scent. A decrease in (unpleasant) odors in the context of this document means a partial reduction or complete reduction, that is to say removal, of (unpleasant) odors by a particular substance or a particular substance mixture, in particular of odors or scents of the technical, metal and/or fatty type or similar odors.

Furthermore, the present invention should indicate new, advantageous fragrance mixtures, in particular perfume oils, which contain such substances. Such fragrance mixtures should in particular be suitable for scenting or perfuming certain products.

Furthermore, correspondingly perfumed products containing such a fragrance mixture and a method for producing such products should be indicated.

Perfuming (of a product) in the strictest sense is different here from reducing an unpleasant odor (as described above) and can also lead to such a reduction. Perfuming means the imparting of an olfactory impression that is to say of an (additional) olfactory effect.

Further objects of the present invention arise from the following statements and the attached claims.

DETAILED DESCRIPTION OF THE INVENTION

To facilitate an understanding of the principles and features of the various embodiments of the invention, various illustrative embodiments are explained below. Although exemplary embodiments of the invention are explained in detail, it is to be understood that other embodiments are contemplated. Accordingly, it is not intended that the invention is limited in its scope to the details of construction and arrangement of components set forth in the following description or illustrated in the drawings. The invention is capable of other embodiments and of being practiced or carried out in various ways. Also, in describing the exemplary embodiments, specific terminology will be resorted to for the sake of clarity.

It must also be noted that, as used in the specification and the appended claims, the singular forms "a," "an" and "the" include plural references unless the context clearly dictates otherwise. For example, reference to a component is intended also to include composition of a plurality of components. References to a composition containing "a" constituent is intended to include other constituents in addition to the one named.

Also, in describing the exemplary embodiments, terminology will be resorted to for the sake of clarity. It is intended that each term contemplates its broadest meaning as understood by those skilled in the art and includes all technical equivalents which operate in a similar manner to accomplish a similar purpose.

Ranges may be expressed herein as from "about" or "approximately" or "substantially" one particular value and/or to "about" or "approximately" or "substantially" another particular value. When such a range is expressed, other exemplary embodiments include from the one particular value and/or to the other particular value.

Similarly, as used herein, "substantially free" of something, or "substantially pure", and like characterizations, can include both being "at least substantially free" of something, or "at least substantially pure", and being "completely free" of something, or "completely pure".

By "comprising" or "containing" or "including" is meant that at least the named compound, element, particle, or method step is present in the composition or article or method, but does not exclude the presence of other compounds, materials, particles, method steps, even if the other such compounds, material, particles, method steps have the same function as what is named.

It is also to be understood that the mention of one or more method steps does not preclude the presence of additional method steps or intervening method steps between those steps expressly identified. Similarly, it is also to be understood that the mention of one or more components in a composition does not preclude the presence of additional components than those expressly identified.

The materials described as making up the various elements of the invention are intended to be illustrative and not restrictive. Many suitable materials that would perform the same or a similar function as the materials described herein are intended to be embraced within the scope of the invention. Such other materials not described herein can include, but are not limited to, for example, materials that are developed after the time of the development of the invention.

In an exemplary embodiment, the present invention comprises the use of a composition comprising:

providing a composition comprising a compound of formula (I)

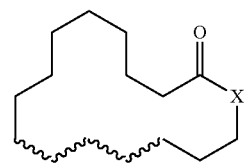

(I)

wherein two or less of the four jagged lines denotes a double bond;
wherein the remaining jagged lines denote a single bond; and
wherein X is selected from the group consisting of —O—, —CH$_2$— and —O—CH$_2$—; and exposing a substance to the composition.

The substance can comprise at least a portion of an odor. The substance need not be a compound of formula (I).

Exposing the composition to the substance can comprise masking at least a portion of an unpleasant olfactory impression of the substance. Exposing the composition to the substance can comprise decreasing at least a portion of an unpleasant olfactory impression of the substance. Exposing the composition to the substance can comprise enhancing at least a portion of a pleasant olfactory impression of the substance.

The compound can be selected from the group consisting of cyclohexadec-8-en-1-one (Aurelione, CAS No. 88642-03-

9, 3100-36-5; Globanone, CAS No. 3100-36-5), cyclohexadecanone (Isomuscone, CAS No. 2550-52-9), oxacyclohexadecen-2-one (Globalide, CAS No. 34902-57-3, 111879-80-2), cyclopentadecanolide (Macrolide, CAS No. 106-02-5) and (9Z)-17-Oxacycloheptadec-9-en-1-one (Ambrettolide, CAS No. 28645-51-4).

The use can comprise providing a plurality of compositions comprising a compound of formula (I) to a plurality of substances of an odor. The use can comprise providing a plurality of different compositions comprising a compound of formula (I) to a plurality of different substances of an odor.

The odor can create an unpleasant olfactory impression selected from the group consisting of fatty, technical and metallic. The odor can create a pleasant olfactory impression selected from the group consisting of natural freshness, radiance and flowery.

The substance can be selected from the group consisting of fragrances with a molecular weight in a range between approximately 150 g/mol to approximately 285 g/mol. The substance can be selected from the group consisting of alcohols, aldehydes, ketones, ethers, esters and carboxylates.

The substance can be selected from the group consisting of methyl dihydrojasmonate, benzyl salicylate, cis-3-hexenyl salicylate, isoamyl salicylate, hexyl salicylate, 2,3,8,8-tetramethyl-1,2,3,4,5,6,7,8-octahydro-2-naphthalenylmethyl ketone, linalyl acetate, ethyllinalyl acetate, cedryl methyl ether, cedryl methyl ketone, cedryl acetate, (4aR,5R,7aS,9R)-octahydro-2,2,5,8,8,9a-hexamethyl-4H-4a,9-methano azuleno(5,6-d)-1,3-dioxol), 1',1',5',5'-tetra methyl -hexahydro-spiro[1.3-dioxolan-2.8'(5'H)-2H-2.4a]methanonaphthalene, cyclododecyl methyl ether, (ethoxymethoxy)cyclododecane, decahydro-beta-naphthyl acetate, 4,7-methano-3a,4,5,6,7,7a-hexahydro-5(-6)-indenyl acetate, allyl-3-cyclohexyl propionate, allylcyclohexyloxy acetate, benzyl benzoate, benzyl cinnamate, 15-hydroxy-Pentadecanonsäurelacton, 3-methyl-cyclopentadecenone, 1,3,4,6,7,8-hexahydro-4,6,6,7,8,8-hexamethyl cyclopenta[g]-2-benzopyrane, 2-[1-(3,3-dimethylcyclohexyl)ethoxy]-2-methyl-,1-propanoate, 1,4-dioxacycloheptadecan-5,17-dione, 3-methyl-cyclopentadecanone, 3a,6,6,9a-tetramethyl dodecahydronaphtho[2,1-b]furan, alpha-irone, beta-irone, alpha-n-methylionone, beta-n -methylionone, alpha-isomethylionone, beta-isomethylionone and allyl ionone, 2-methyl-3-(4-tert-butylphenyl)propanal, 4-(4-hydroxy-4-methylpentyl)-3-cyclohexencarboxaldehyde, 2-methyl-4-(2,6,6-trimethyl-1-cyclohexen-1-yl)-2-butenal, 1-methyl-4-(4-methyl-3-penten-1-yl)-3-cyclohexencarboxaldehyde, 3-(3-isopropyl-phenyl)-butyraldehyde, (E)-2,6,10-trimethyl-undeca-5,9-dienal, benzo[1,3]dioxole-5-carbaldehyde, 2,2-dimethyl-3-phenyl-propan-1-ol, 2,2-dimethyl-3-m-tolyl-propan-1-ol, 1-(4-isopropyl-cyclohexyl)-ethanol, (4-isopropyl-cyclohexyl)-methanol, 2-phenyl-ethanol, 2-isobutyl-4-methyl-tetrahydro-pyran-4-ol, 3,7-dimethyl-octa-1,6-dien-3-ol, (Z)-3,7-dimethyl-octa-2,6-dien-1-ol, (E)-3,7-dimethyl-octa-2,6-dien-1-ol, 3,7-dimethyl-oct-6-en-1-ol, 2,6-dimethyl-oct-7-en-2-ol, 3,7-dimethyl-octan-1-ol, 2-methyl-6-methylenoct-7-en-2-ol and (E/Z)-3,7-dimethyl-nona-1,6-dien-3-ol.

The ratio of the mass of the substance(s) to the mass of the composition(s) can greater than or equal to 99:1. The ratio of the mass of the substance to the mass of the composition can be greater than or equal to 99.9:0.1. The ratio of the mass of the substance to the mass of the composition can greater than or equal to 99.999:0.001.

The quantity of composition is not sufficient to impart a musk odor.

In another exemplary embodiment, the present invention comprises a first compound of formula (I)

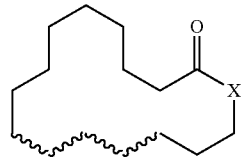

(I)

wherein two or less of the four jagged lines denotes a double bond;

wherein the remaining jagged lines denote a single bond; and wherein X is selected from the group consisting of —O—, —CH$_2$— and —O—CH$_2$—; and a second compound not of the formula (I);

wherein the second compound has a molecular weight in a range between approximately 150 g/mol to approximately 285 g/mol; and wherein the ratio of the mass of the second compound to the mass of the first compound is greater than or equal to 99:1.

The ratio of the mass of the second compound to the mass of the first compound can greater than or equal to 99.9:0.1. The ratio of the mass of the second compound to the mass of the first compound can greater than or equal to 99.999:0.001.

The composition can comprise a plurality of first compounds and a plurality of compounds not of the formula (I).

The composition can comprise a fragrance mixture.

The first compound of formula (I) can be selected from the group consisting of cyclohexadec-8-en-1-one (Aurelione, CAS No. 88642-03-9, 3100-36-5; Globanone, CAS No. 3100-36-5), cyclohexadecanone (Isomuscone, CAS No. 2550-52-9), oxacyclohexadecen-2-one (Globalide, CAS No. 34902-57-3, 111879-80-2), cyclopentadecanolide (Macrolide, CAS No. 106-02-5) and (9Z)-17-oxacycloheptadec-9-en-1-one (Ambrettolide, CAS No. 28645-51-4).

The second compound can be selected from the group consisting of methyl dihydrojasmonate, benzyl salicylate, cis-3-hexenyl salicylate, isoamyl salicylate, hexyl salicylate, 2,3,8,8-tetramethyl-1,2,3,4,5,6,7,8-octahydro-2-naphthalenylmethyl ketone, linalyl acetate, ethyllinalyl acetate, cedryl methyl ether, cedryl methyl ketone, cedryl acetate, (4aR,5R,7aS,9R)-octahydro-2,2,5,8,8,9a-hexamethyl-4H-4a,9-methano azuleno (5,6-d)-1,3-dioxol), 1',1',5',5'-tetra methyl-hexahydro-spiro[1.3-dioxolan-2.8'(5'H)-2H-2.4a]methanonaphthalene, cyclododecyl methyl ether, (ethoxymethoxy)cyclododecane, decahydro-beta-naphthyl acetate, 4,7-methano-3a,4,5,6,7,7a-hexahydro-5(-6)-indenyl acetate, allyl-3-cyclohexyl propionate, allylcyclohexyloxy acetate, benzyl benzoate, benzyl cinnamate, 15-hydroxy-Pentadecanonsäurelacton, 3-methyl-cyclopentadecenone, 1,3,4,6,7,8-hexahydro-4,6,6,7,8,8-hexamethyl cyclopenta[g]-2-benzopyrane, 2-[1-(3,3-dimethylcyclohexyl)ethoxy]-2-methyl-,1-propanoate, 1,4-dioxacycloheptadecan-5,17-dione, 3-methyl-cyclopentadecanone, 3a,6,6,9a-tetramethyl dodecahydronaphtho[2,1-b]furan, alpha-irone, beta-irone, alpha-n-methylionone, beta-n-methylionone, alpha-isomethylionone, beta-isomethylionone and allyl ionone, 2-methyl-3-(4-tert-butylphenyl)propanal, 4-(4-hydroxy-4-methylpentyl)-3-cyclohexencarboxaldehyde, 2-methyl-4-(2,6,6-trimethyl-1-cyclohexen-1-yl)-2-butenal, 1-methyl-4-(4-methyl-3-penten-1-yl)-3-cyclohexencarboxaldehyde, 3-(3-isopropyl-phenyl)-butyraldehyde, (E)-2,6,10-trimethyl-undeca-5,9-dienal, benzo[1,3]dioxole-5-carbaldehyde, 2,2-dimethyl-3-phenyl-propan-1-ol, 2,2-dimethyl-3-m-tolyl-propan-1-ol, 1-(4-isopropyl-cyclohexyl) -ethanol, (4-isopropyl-cyclohexyl)-methanol, 2-phenyl-ethanol, 2-isobutyl-4-methyl-tetrahydro-pyran-4-ol, 3,7-dimethyl-octa-1,6-dien-3-ol, (Z)-3,7-dimethyl-octa-2,6-dien-1-ol, (E)-3,7-dimethyl-octa-2,6-dien-1-ol, 3,7-dimethyl-oct-6-en-1-ol, 2,6-dimethyl-oct-7-en-2-ol, 3,7-dimethyl-octan-1-ol, 2-methyl-6-methylenoct-7-en-2-ol and (E/Z)-3,7-dimethyl-nona-1,6-dien-3-ol.

The proportion of the first compound(s) of formula (I) in relation to the total weight of the fragrance mixture can be 1 wt. % or less. The proportion of the first compound of formula (I) in relation to the total weight of the fragrance mixture can be 0.1 wt. % or less. The proportion of the first compound of formula (I) in relation to the total weight of the fragrance mixture can be 0.001 wt. % or less.

In another exemplary embodiment, the present invention comprises a perfumed product containing a sensorially effective quantity of a fragrance mixture, wherein the proportion of the fragrance mixture in relation to the total mass of the product is in a range between approximately 0.01 to approximately 10 wt %. The proportion of the fragrance mixture in relation to the total mass of the product can be in a range between approximately 0.1 to approximately 5 wt %. The proportion of the fragrance mixture in relation to the total mass of the product can be in a range between approximately 0.25 to approximately 3 wt %.

The perfumed product can be selected from the group consisting of perfume extracts, eaux de parfum, eaux de toilettes, aftershaves, eaux de colognes, pre-shave products, splash colognes, perfumed freshening wipes, acidic, alkaline and neutral cleaners, textile fresheners, ironing aids, liquid laundry detergents, pulverulent laundry detergents, laundry pretreatment agents, fabric softeners, washing soaps, washing tablets, disinfectants, surface disinfectants, air fresheners, aerosol sprays, waxes and polishes, body care compositions, hand creams and lotions, foot creams and lotions, depilatory creams and lotions, aftershave creams and lotions, tanning creams and lotions, hair care products, deodorants and antiperspirants, products in decorative cosmetics, candles, lamp oils, joss-sticks, insecticides, repellents and propellants.

Thus, a primary object of the present invention is achieved by the use of
(i) an individual compound of formula (I) or
(ii) a mixture comprising or consisting of two or a plurality of compounds of formula (I)

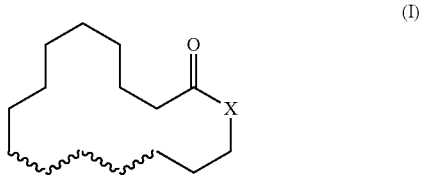

(I)

wherein for the compound of formula (I) or for each compound of formula (I) it is the case that
  none, one or two of the four jagged lines denotes or denote a double bond and the other jagged lines in each case denote a single bond and
  X is selected from between —O—, —CH$_2$— and —O—CH$_2$—, preferably from between —O— and —CH$_2$,
(a) for masking or decreasing the or one or a plurality of unpleasant olfactory impressions of one or a plurality of substances with an unpleasant odor, wherein the substance(s) is or are not a compound of formula (I), and/or
(b) for enhancing the or one or a plurality of pleasant olfactory impressions of one or a plurality of substances with a pleasant odor, wherein the substance(s) is or are not a compound of formula (I).

Compounds of general formula (I) are basically known to a person skilled in the art. A description of the olfactory characteristics of formula (I) can also be found, inter alia, in the reference book "S. Arctander, Perfume and Flavor Materials, Vol. I and II, Montclair, N.J., 1969, author's edition" or H. Surburg, J. Panten, Common Fragrance and Flavor Materials, 5th. Ed., Wiley-VCH, Weinheim 2006. The effects described herein, upon which the present invention is based, of such compounds or mixtures, in particular in combination with certain further fragrances (as described in the following) were unknown up until now.

Surprisingly, the compounds of general formula (I), cause certain desired olfactory aspects of other substances to be intensified or accentuated/enhanced and/or certain undesired olfactory aspects of other substances to be masked or decreased, preferably fatty, metallic and/or (chemical) technical notes of other (olfactory) substances, in particular the fragrances described herein.

The compounds to be used according to the invention of formula (I) are also advantageously easy to access or manufacture, are highly effective even at low concentrations, in particular at concentrations in which the compounds of formula (I) have no or at least a hardly noticeable characteristic odor, are extensively or completely colorless, have a high stability in different mixtures or preparations and have no toxic and/or allergenic effect in humans.

Compounds of formula (I) also have the advantage that in use, in particular in use according to the invention, they can be combined with various fragrances and perfume oils or the normal ingredients of a perfume oil, in order to perfume products with any fragrance. Accordingly, the present invention allows a broad selection of scent types to be offered to consumers. Fragrance mixtures and perfumed products according to the invention containing one or a plurality of compound(s) of formula (I) are described in the following.

As described above, compounds of formula (I) according to a preferred aspect of the present invention are in particular suitable for masking or decreasing, in particular for decreasing, the or one or a plurality of unpleasant olfactory impressions of one or a plurality of substances with an unpleasant odor, not corresponding to formula (I). The "substances with an unpleasant odor" mentioned here can also have other, generally not unpleasant sensorial qualities, including also olfactory qualities. "Substances with an unpleasant odor" within the context of this document therefore generally means substances that bring about one or a plurality of unpleasant olfactory impressions, be these primary odors or ancillary/subsidiary scents. The substances with an unpleasant odor described herein can in particular be those substances which first of all are perceived as substances with a pleasant odor, but which (also) have a metallic, fatty and/or technical note, which according to the invention it is preferable to reduce. The same applies by analogy to the "substances with a pleasant odor" described herein. That is to say that "substances with a pleasant odor" in the context of the present document are generally understood to be substances which generate one or a plurality of pleasant olfactory impressions, be these as primary odor or ancillary/subsidiary scent. As a result in the context of the present invention for example both an unpleasant scent of a certain substance (with an unpleasant odor) can be masked or decreased, and a pleasant scent of the same substance (also with a pleasant odor) can be enhanced.

Preference according to the invention is a use as described above, wherein (i) the compound of formula (I) or (ii) one, a plurality of or all compounds of formula (I) is or are selected from the group consisting cyclohexadec-8-en-1-one (Aurelione, CAS No. 88642-03-9, 3100-36-5; Globanone, CAS No. 3100-36-5), cyclohexadecanone (Isomuscone, CAS No. 2550-52-9), oxacyclohexadecen-2-one (Globalide, CAS No. 34902-57-3, 111879-80-2), cyclopentadecanolide (Macrolide, CAS No. 106-02-5) and (9Z)-17-oxacycloheptadec-9-en-1-one (Ambrettolide, CAS No. 28645-51-4).

The compounds to be used according to the invention of formula (I) and mixtures are in particular suitable
(a) for masking or decreasing the or one or a plurality of unpleasant olfactory impressions of one or a plurality of substances with an unpleasant odor, wherein the substance(s) is or are not a compound of formula (I), wherein the or one, a plurality of or all of the unpleasant olfactory impressions is or are selected from fatty, technical and metallic,
and/or
(b) for enhancing the or one or a plurality of pleasant olfactory impressions of one or a plurality of substances with a pleasant odor, wherein the substance(s) is or are not a compound of formula (I), namely for intensifying or improving the natural freshness and/or radiance of one or a plurality of substances with a pleasant odor and/or to intensify the or a flowery scent of one or a plurality of substances with a pleasant odor, in particular a jasmine type scent.

The or one, a plurality of or all substances, whose olfactory characteristics are improved according to the invention by use of one or a plurality of compounds of formula (I), is or are preferably fragrances with a flowery note, in particular of the jasmine type.

Preference is basically for such a use according to the invention, wherein the or one, a plurality of or all of the substance(s) with a pleasant and/or unpleasant odor not corresponding to formula (I) is or are selected from the group consisting of fragrances with a molecular weight in the range 150 g/mol through 285 g/mol, in particular alcohols, aldehydes, ketones, ethers, esters and carboxylates, in particular alcohols, aldehydes, ketones, ethers and esters, with a molecular weight in the range 150 g/mol through 285 g/mol.

Special preference is for substances, in particular alcohols and aldehydes, with a molecular weight of 210 g/mol or less and substances, in particular ketones, ethers and esters, with a molecular weight in the range 190 g/mol through 250 g/mol.

In the context of the present invention a use (as described above) particularly preferred, wherein the or one, a plurality of or all of the substance(s) with a pleasant and/or unpleasant odor not corresponding to formula (I) is or are selected from the group consisting of methyl dihydrojasmonate, benzyl salicylate, cis-3-hexenyl salicylate, isoamyl salicylate, hexyl salicylate, 2,3,8,8-tetramethyl-1,2,3,4,5,6,7,8-octahydro-2-naphthalenylmethyl ketone, linalyl acetate, ethyllinalyl acetate, cedryl methyl ether, cedryl methyl ketone, cedryl acetate, (4aR,5R,7aS,9R)-octahydro-2,2,5,8,8,9a-hexamethyl-4H-4a,9-methano azuleno (5,6-d)-1,3-dioxol), 1',1',5',5'-tetra methyl-hexahydro-spiro[1.3-dioxolan-2.8'(5'H)-2H-2.4a]methanonaphthalene, cyclododecyl methyl ether, (ethoxymethoxy)cyclododecane, decahydro-beta-naphthyl acetate, 4,7-methano-3a,4,5,6,7,7a-hexahydro-5(-6)-indenyl acetate, allyl-3-cyclohexyl propionate, allylcyclohexyloxy acetate, benzyl benzoate, benzyl cinnamate, 15-hydroxy-Pentadecanonsäurelacton, 3-methyl-cyclopentadecenone, 1,3,4,6,7,8-hexahydro-4,6,6,7,8,8-hexamethyl cyclopenta[g]-2-benzopyrane, 2-[1-(3,3-dimethylcyclohexyl)ethoxy]-2-methyl-, 1-propanoate, 1,4-dioxacycloheptadecan-5,17-dione, 3-methyl-cyclopentadecanone, 3a,6,6,9a-tetramethyl dodecahydronaphtho[2,1-b]furan, alpha-irone, beta-irone, alpha-n-methylionone, beta-n-methylionone, alpha-isomethylionone, beta-isomethylionone and allyl ionone, 2-methyl-3-(4-tert-butylphenyl)propanal, 4-(4-hydroxy-4-methylpentyl)-3-cyclohexencarboxaldehyde, 2-methyl-4-(2,6,6-trimethyl-1-cyclohexen-1-yl)-2-butenal, 1-methyl-4-(4-methyl-3-penten-1-yl)-3-cyclohexencarboxaldehyde, 3-(3-isopropyl-phenyl) -butyraldehyde, (E)-2,6,10-trimethyl-undeca-5,9-dienal, benzo[1,3]dioxole-5-carbaldehyde, 2,2-dimethyl-3-phenyl-propan-1-ol, 2,2-dimethyl-3-m-tolyl-propan-1-ol, 1-(4-isopropyl-cyclohexyl) -ethanol, (4-isopropyl-cyclohexyl)-methanol, 2-phenyl-ethanol, 2-isobutyl-4-methyl-tetrahydro -pyran-4-ol, 3,7-dimethyl-octa-1,6-dien-3-ol, (Z)-3,7-dimethyl-octa-2,6-dien-1-ol, (E)-3,7-dimethyl-octa-2,6-dien-1-ol, 3,7-dimethyl-oct-6-en-1-ol, 2,6-dimethyl-oct-7-en-2-ol, 3,7-dimethyl-octan-1-ol, 2-methyl-6-methylenoct-7-en-2-ol and (E/Z)-3,7-dimethyl-nona-1,6-dien-3-ol.

Advantageously the compounds to be used according to the invention of formula (I), in particular those indicated herein as preferred, are particularly suited to masking or decreasing the or one, a plurality of or all the unpleasant olfactory impressions fatty, technical and metallic of the abovementioned (olfactory) substances and/or to enhancing or improving the natural freshness and/or radiance of these (olfactory) substances and/or to enhance a flowery scent, in particular a scent of the jasmine type, of these (olfactory) substances.

Particularly advantageous is a use according to the invention, wherein the ratio of the total mass of substances with a pleasant and/or unpleasant odor not corresponding to formula (I) to the total mass of compound(s) of formula (I) is greater than or equal to 99:1, preferably greater than or equal to 99.9:0.1, particularly preferably greater than or equal to 99.999:0.001.

For the purposes of the present invention a use according to the invention is also particularly suitable, wherein the quantity of compound(s) of formula (I) used for decreasing or masking and/or for enhancing is not sufficient to impart a characteristic odor, in particular a musk odor. For the compounds preferred according to the invention of formula (I) have the advantage that in use, in particular in a use according to the invention, they are effective in such low concentrations for the purposes of the present invention, that no or at least no perceptible characteristic odor of the compounds of formula (I) is imparted. As a result these compounds can be combined with various fragrances and possibly further ingredients of a perfume oil, in order to produce particularly advantageous fragrance mixtures or to perfume products with any scent.

In the following fragrance mixtures according to the invention are described.

Accordingly, a further aspect of the present invention concerns a fragrance mixture, preferably a perfume oil, comprising or consisting of
(A) (i) an individual compound of formula (I) or
(ii) a mixture comprising or consisting of two or a plurality of compounds of formula (I)

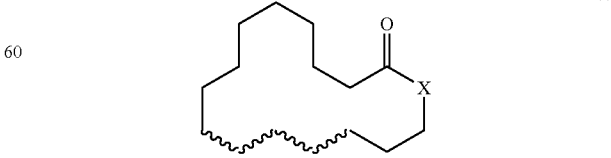

(I)

wherein for the compound of formula (I) or for each compound of formula (I) it is the case that none, one or two of the four jagged lines denotes or denote a double bond and the other jagged lines in each case denote a single bond and X is selected from —O—, —CH$_2$— and —O—CH$_2$—, in particular from —O— and —CH$_2$—, and (B) one, two, three, four, five, six or a plurality of (further) fragrances, wherein the (further) fragrance(s) is (are) not a compound or compounds of formula (I) and one, two, three, four, five, six or a plurality of or all the (further) fragrances has or have a molecular weight in the range 150 g/mol through 285 g/mol, characterized in that the ratio of the total mass of fragrances not corresponding to formula (I) to the total mass of compound or compounds of formula (I) is greater than or equal to 99:1, preferably greater than or equal to 99.9:0.1, particularly preferably greater than or equal to 99.999:0.001.

For the preferably used or contained compounds of formula (I) or mixtures of these that stated above applies by analogy. For the fragrances according to ingredient (B) that stated above concerning the substances with an unpleasant and/or pleasant odor not corresponding to formula (I) preferably applies by analogy.

A person skilled in the art in a fragrance mixture according to the invention (for example a perfume oil) will select the proportion of component (A), that is to say the proportion of compounds of formula (I), in consideration of the present document, such that the desired effect of intensifying/enhancing (accentuating) and/or masking or decreasing a scent is achieved, wherein care will be taken not to use an excessive quantity of component (A), which could dominate the sensorial overall impression of a fragrance mixture and on the other hand not to provide for merely such as small quantity of component (A) that an intensification or masking or decreasing of olfactory aspects of fragrances of component (B) cannot or can hardly be noticed any longer.

Particularly preferable quantity ratios according to the invention arise from the configurations below and in particular from the attached examples.

Fragrance mixtures according to the invention are usually liquid at 25° C. and 1013hPa and as a rule homogenous solutions.

Fragrance mixtures, in particular perfume oils, often comprise synthetic or natural (preferably) tasteless and odorless carrier oils, which contain the scents or fragrances (as synthetic or natural substances) in highly concentrated form (and possibly perfuming solvents and/or adjuvants).

Perfume oils are often used for scent applications. With perfume oils for example perfumes are produced, by adding these in (for example alcoholic) solutions, which upon evaporation "draw with them" the scents or fragrances thereby imparting to the olfactory organ of the user, that is to say of the person, the sensation of a particular odor. Such mixtures can for example be a perfume, eau de parfum or eau de toilette. Perfume oils are also used to create a certain scent in living spaces, such as for example when used in aroma lamps, atomizers or diffusers. Furthermore, however, perfume oils can also be used in numerous other articles or preparations, for example ranging from sun creams to hair shampoos, from to sanitary towels to toilet cleaners, from face crèmes to washing powders and cat litter.

A fragrance mixture according to invention, in addition to ingredients (A) and (B) (as described above) can contain one or a plurality of further (normal) ingredients or substances, including one or a plurality of further fragrances not corresponding to the above criteria of ingredient (B).

Examples of fragrances, which can basically advantageously be used as an ingredient of a fragrance mixture according to the invention, in particular a perfume oil according to the invention, can be found for example in S. Arctander, Perfume and Flavor Chemicals, Vol. I and II, Montclair, N.J., 1969, author's edition or H. Surburg, J. Panten, Common Fragrance and Flavor Materials, 5$^{th}$ Ed., Wiley-VCH, Weinheim 2006.

Preferred essential oils, concretes, absolutes, resins, resinoids, balsams and/or tinctures, which can be an ingredient of a fragrance mixture according to the invention, in particular a perfume oil according to the invention, are preferably selected from the group consisting of:

ambergris tincture; amyris oil; angelica seed oil; angelica root oil; anise oil; valerian oil; basil oil; wood moss absolute; bay oil; mugwort oil; benzoin resin; bergamot oil; beeswax absolute; birch tar oil; bitter almond oil; savory oil; bucco leaf oil; cabreuva oil; cade oil; calmus oil; camphor oil; cananga oil; cardamom oil; cascarilla oil; cassia oil; cassia absolute; castoreum absolute; cedar leaf oil; cedarwood oil; cistus oil; citronella oil; lemon oil; copaiva balsam; copaiva balsam oil; coriander oil; costus root oil; cumin oil; cypress oil; davana oil; dill herb oil; dill seed oil; eau de brouts absolute; oakmoss absolute; elemi oil; estragon oil; eucalyptus citriodora oil; eucalyptus oil; fennel oil; spruce needle oil; galbanum oil; galbanum resin; geranium oil; grapefruit oil; guaiac wood oil; gurjun balsam; gurjun balsam oil; helichrysum absolute; helichrysum oil; ginger oil; iris root absolute; iris root oil; jasmine absolute; calamus oil; camomile blue oil; camomile Roman oil; carrot seed oil; cascarilla oil; pine needle oil; spearmint oil; caraway oil; labdanum oil; labdanum absolute; labdanum resin; lavandin absolute; lavandin oil; lavender absolute; lavender oil; lemongrass oil; lavage oil; distilled lime oil; pressed lime oil; linaloe oil; litsea cubeba oil; bayleaf oil; mace oil; marjoram oil; mandarin oil; massoi bark oil; mimosa absolute; musk seed oil; musk tincture; clary sage oil; nutmeg oil; myrrh absolute; myrrh oil; myrtenol; clove leaf oil; clove flower oil; neroli oil; olibanum absolute; olibanum oil; opopanax oil; orange-flower absolute; orange oil; origanum oil; palmarosa oil; patchouli oil; perilla oil; peruvian balsam oil; parsley leaf oil; parsley seed oil; petitgrain oil; peppermint oil; pepper oil; pimenta oil; pine oil; pennyroyal oil; rose absolute; rosewood oil; rose oil; rosemary oil; dalmation sage oil; Spanish sage oil; sandalwood oil; celery seed oil; spike lavender oil; Japanese anise oil; styrax oil; tagetes oil; fir needle oil; teatree oil; turpentine oil; thyme oil; tolu balsam; tonka absolute; tuberose absolute; vanilla extract; violet leaf absolute; verbena oil; vetiver oil; juniper oil; wine lees oil; absinthe oil; wintergreen oil; ylang oil; hyssop oil; civet absolute; cinnamon leaf oil; cinnamon bark oil.

Preferred individual fragrances, which can preferably be used as an ingredient of a fragrance mixture according to the invention, in particular a perfume oil according to the invention, are selected from the group of hydrocarbons, with preference here for 3-carene; alpha-pinene; beta-pinene; alpha-terpinene; gamma-terpinene; p-cymene; bisabolene; camphene; caryophyllene; cedrene; farnesene; limonene; longifolene; myrcene; ocimene; valencene; (E,Z)-1,3,5-undecatriene; styrene; diphenylmethane;

the aliphatic alcohols, with preference here for hexanol; octanol; 3-octanol; 2,6-dimethyl-heptanol; 2-methyl-2-heptanol; 2-methyl-2-octanol; (E)-2-hexenol; (E)- and (Z)-3-hexenol; 1-octen-3-ol; a mixture of 3,4,5,6,6-pentamethyl-3/4-hepten-2-ol and 3,5,6,6-tetramethyl-4-methyleneheptan-2- ol; (E,Z)-2,6-nonadienol; 3,7-dimethyl-7-methoxyoctan-2-ol; 9-dec enol; 10-undecenol; 4-methyl-3-decen-5-ol;

the aliphatic aldehydes and their acetals, with preference here for hexanal; heptanal; octanal; nonanal; decanal; undecanal; dodecanal; tridecanal; 2-methyloctanal; 2-methylnonanal; (E)-2-hexenal; (Z)-4-heptenal; 2,6-dimethyl-5-heptenal; 10-undecenal; (E)-4-decenal; 2-do decenal; 2,6,10-trimethyl-5,9-undecadienal; heptanal-diethylacetal; 1,1-dimethoxy-2,2,5-trimethyl-4-hexene; citronellyl oxyacetaldehyde; 1-(1-methoxy-propoxy)-(E/Z)-3-hexene;

the aliphatic ketones and oximes thereof, with preference here for 2-heptanone; 2-octanone; 3-octanone; 2-nonanone; 5-methyl-3-heptanone; 5-methyl-3-heptanone oxime; 2,4,4,7-tetramethyl-6-octen-3-one; 6-methyl-5-hepten-2-one;

the aliphatic sulfur-containing compounds, with preference here for 3-methylthiohexanol; 3-methylthiohexyl acetate; 3-mercaptohexanol; 3-mercaptohexyl acetate; 3-mercaptohexyl butyrate; 3-acetyltbiohexyl acetate; 1-menthene-8-thiol;

the aliphatic nitriles, with preference here for 2-nonenenitrile; 2-undecenenitrile; 2-tridecenenitrile; 3,12-tridecenenitrile; 3,7-dimethyl-2,6-octadienenitrile; 3,7-dimethyl-6-octenenitrile;

the aliphatic carboxylic acid esters, with preference here for (E)- and (Z)-3-hexenylformate; ethyl acetoacetate; isoamyl acetate; hexyl acetate; 3,5,5-trimethylhexyl acetate; 3-methyl-2-butenyl acetate; (E)-2-hexenyl acetate; (E)- and (Z)-3-hexenyl acetate; octyl acetate; 3-octyl acetate; 1-octen-3-yl acetate; ethyl butyrate; butyl butyrate; isoamyl butyrate; hexylbutyrate; (E)- and (Z)-3-hexenyl isobutyrate; hexyl crotonate; ethylisovalerate; ethyl-2-methyl pentanoate; ethyl hexanoate; allyl hexanoate; ethyl heptanoate; allyl heptanoate; ethyl octanoate; ethyl-(E,Z)-2,4-decadienoate; methyl-2-octinate; methyl-2-noninate; allyl-2-isoamyl oxyacetate; methyl-3,7-dimethyl-2,6-octadienoate; 4-methyl-2-pentyl-crotonate;

the acyclic terpene alcohols, with preference here for citronellol; geraniol; nerol; linalool; lavandulol; nerolidol; farnesol; tetrahydrolinalool; tetrahydrogeraniol; 2,6-dimethyl-7-octen-2-ol; 2,6-dimethyloctan-2-ol; 2-methyl-6-methylene-7-octen-2-ol; 2,6-dimethyl-5,7-octadien-2-ol; 2,6-dimethyl-3,5-octadien-2-ol; 3,7-dimethyl-4,6-octadien-3-ol; 3,7-dimethyl-1,5,7-octatrien-3-ol 2,6-dimethyl-2,5,7-octatrien-1-ol; as well as formates, acetates, propionates, isobutyrates, butyrates, isovalerates, pentanoates, hexanoates, crotonates, tiglinates and 3-methyl-2-butenoates thereof;

the acyclic terpene aldehydes and ketones, with preference here for geranial; neral; citronellal; 7-hydroxy-3,7-dimethyloctanal; 7-methoxy-3,7-dimethyloctanal; 2,6,10-trimethyl-9-undecenal; geranylacetone; as well as the dimethyl- and diethylacetals of geranial, neral and 7-hydroxy-3,7-dimethyloctanal;

the cyclic terpene alcohols, with preference here for isopulegol; alpha-terpineol; terpinen-4-ol; menthan-8-ol; menthan-1-ol; menthan-7-ol; borneol; isoborneol; linalool oxide; nopol; cedrol; ambrinol; vetiverol; guaiol; and their formates, acetates, propionates, isobutyrates, butyrates, isovalerates, pentanoates, hexanoates, crotonates, tiglinates and 3-methyl-2-butenoates; menthyl formiate; menthyl propionate; menthyl butyrate; menthyl isobutyrate; menthyl isovalerianate; menthyl hexanoate; menthyl crotonate; menthyl tiglinate;

the cyclic terpene aldehydes and ketones, with preference here for menthone; isomenthone; 8-mercaptomenthan-3-one; carvone; camphor; fenchone; alpha-ionone; beta-ionone; beta-n-methylionone; beta-isomethylionone; alpha-ironone; alpha-damascone; beta-damascone; beta-damascenone; delta-damascone; gamma-damascone; 1-(2,4,4-trimethyl-2-cyclohexen-1-yl)-2-buten-1-one; 1,3,4,6,7,8a-hexahydro-1,1,5,5-tetramethyl-2H-2,4a -methanonaphthalen-8 (5H-)-one; 2-methyl-4-(2,6,6-trimethyl-1-cyclohexen-1-yl)-2-butenal; nootkatone; dihydronootkatone; 4,6,8-megastigmatrien-3-one; alpha-sinensal; beta-sinensal; acetylated cedarwood oil (cedryl methyl ketone);

the cyclic alcohols, with preference here for 4-tert.-butylcyclohexanol; 3,3,5-trimethylcyclohexanol; 3-isocamphylcyclohexanol; 2,6,9-trimethyl-Z2,Z5,E9-cyclododecatrien-1-ol; 2-isobutyl-4-methyltetrahydro-2H-pyran-4-ol;

the cycloaliphatic alcohols, with preference here for alpha,3,3-trimethylcyclo-hexyl -methanol; 1-(4-isopropylcyclohexyl)ethanol; 2-methyl-4-(2,2,3-trimethyl-3-cyclopent-1-yl)butanol; 2-methyl-4-(2,2,3-trimethyl-3-cyclopent-1-yl)-2-buten-1-ol; 2-ethyl-4-(2,2,3-trimethyl-3-cyclopent-1-yl)-2-buten-1-ol; 3-methyl-5-(2,2,3-trimethyl-3-cyclopent-1-yl)-pentan-2-ol; 3-methyl-5-(2,2,3-trimethyl-3-cyclopent-1-yl)-4-penten-2-ol; 3,3-dimethyl-5-(2,2,3-trimethyl-3-cyclopent-1-yl)-4-penten-2-ol; 1-(2,2,6-trimethylcyclohexyl)pentan-3-ol; 1-(2,2,6-trimethylcyclohexyl)hexan-3-ol;

the cyclic and cycloaliphatic ethers, with preference here for cineole; cedryl methyl ether; cyclododecyl methyl ether; 1,1-dimethoxycyclododecane; (ethoxymethoxy)cyclododecane; alpha-cedrene epoxy resin; 3a,6,6,9a-tetramethyl-dodecahydronaphtho[2,1-b]furan; 3a-ethyl-6,6,9a-trimethyl-dodecahydronaphtho[2,1-b]furan; 1,5,9-trimethyl-13-oxabicyclo[10.1.0]-tridea-4,8-diene; rose oxide; 2-(2,4-dimethyl-3-cyclohexen-1-yl)-5-methyl-5-(1-methyl-propyl)-1,3-dioxane;

the cyclic and macrocyclic ketones, with preference here for 4-tert.-butylcyclohexanone; 2,2,5-trimethyl-5-pentylcyclopentanone; 2-heptylcyclopentanone; 2-pentylcyclopentanone; 2-hydroxy-3-methyl-2-cyclopenten-1-one; 3-methyl-cis-2-penten-1-yl-2-cyclopenten-1-one; 3-methyl-2-pentyl-2-cyclopenten-1-one; 3-methyl-4-cyclopentadecenone; 3-methyl-5-cyclopentadecenone; 3-methylcyclopentadecanone; 4-(1-ethoxyvinyl)-3,3,5,5-tetramethylcyclohexanone; 4-tert.-pentylcyclohexanone; 5-cyclohexadecen-1-one; 6,7-dihydro-1,1,2,3,3-pentamethyl-4 (5H)-indanone; 8-cyclohexadecen-1-one; 9-cycloheptadecen-1-one; cyclopentadecanone; cyclohexadecanone;

the cycloaliphatic aldehydes, with preference here for 2,4-dimethyl-3-cyclohexenecarbaldehyde; 2-methyl-4-(2,2,6-trimethyl-cyclohexen-1-yl)-2-butenal; 4-(4-hydroxy-4-methylpentyl)-3-cyclohexenecarbaldehyde; 4-(4-methyl-3-penten-1-yl)-3-cyclohexenecarbaldehyde;

the cycloaliphatic ketones, with preference here for 1-(3,3-dimethylcyclohexyl)-4-penten-1-one; 2,2-dimethyl-1-(2,4-dimethyl-3-cyclohexen-1-yl)-1-propanone; 1-(5,5-dimethyl-1-cyclohexen-1-yl)-4-penten-1-one; 2,3,8,8-tetramethyl-1,2,3,4,5,6,7,8-octahydro-2-naphthalenyl methyl ketone; methyl 2,6,10-trimethyl-2,5,9-cyclododecatrienyl ketone; tert.-butyl (2,4-dimethyl-3-cyclohexen-1-yl) ketone;

the esters of cyclic alcohols, with preference here for 2-tert-butyl cyclohexyl acetate; 4-tert-butyl cyclohexyl acetate; 2-tert-pentyl cyclohexyl acetate; 4-tert-pentyl cyclohexyl acetate; 3,3,5-trimethylcyclohexyl acetate; decahydro-2-naphthyl acetate; 2-cyclopentylcyclopentylcrotonate; 3-pentyltetrahydro-2H-pyran-4-yl acetate; decahydro-2,5,5,8a -tetramethyl-2-naphthyl acetate; 4,7-methano-3a,4,5,6,7,7a-hexahydro-5, or 6-indenyl acetate; 4,7-methano-3a,4,5,6,7,7a-hexahydro-5, or 6-indenyl propionate; 4,7-methano-3a, 4,5,6,7,7a -hexahydro-5, or 6-indenyl isobutyrate; 4,7-methanooctahydro-5, or 6-indenyl acetate;

the esters of cycloaliphatic alcohols, preferably 1-cyclohexyl ethyl crotonate;

the esters of cycloaliphatic carboxylic acids, with preference here for allyl 3-cyclohexylpropionate; allyl cyclohexyloxyacetate; cis- and trans-methyldihydrojasmonate; cis- and trans-methyljasmonate; methyl 2-hexyl-3-oxocyclopentanecarboxylate; ethyl 2-ethyl-6,6-dimethyl-2-cyclohexenecarboxylate; ethyl 2,3,6,6-tetramethyl-2-cyclohexenecarboxylate; ethyl 2-methyl-1,3-dioxolan-2-acetate;

the araliphatic alcohols, with preference here for benzyl alcohol; 1-phenylethyl alcohol; 2-phenylethyl alcohol; 3-phenylpropanol; 2-phenylpropanol; 2-phenoxyethanol; 2,2-dimethyl-3-phenylpropanol; 2,2-dimethyl-3-(3-methylphenyl)propanol; 1,1-dimethyl-2-phenylethyl alcohol; 1,1-dimethyl-3-phenylpropanol; 1-ethyl-1-methyl-3-phenylpropanol; 2-methyl-5-phenylpentanol; 3-methyl-5-phenylpentanol; 3-phenyl-2-propen-1-ol; 4-methoxybenzyl alcohol; 1-(4-isopropylphenyl)ethanol;

the esters of araliphatic alcohols and aliphatic carboxylic acids, with preference here for benzyl acetate; benzyl propionate; benzyl isobutyrate; benzyl isovalerate; 2-phenylethyl acetate; 2-phenylethyl propionate; 2-phenylethyl isobutyrate; 2-phenylethyl isovalerianate; 1-phenylethyl acetate; alpha-trichloromethylbenzyl acetate; alpha,alpha-dimethylphenylethyl acetate; alpha,alpha-dimethylphenylethyl butyrate; cinnamyl acetate; 2-phenoxyethyl isobutyrate; 4-methoxybenzyl acetate;

the araliphatic ethers, with preference here for 2-phenylethyl methyl ether; 2-phenylethyl isoamyl ether; 2-phenylethyl 1-ethoxyethyl ether; phenylacetaldehydedimethylacetal; phenylacetaldehydediethylacetal; hydratropaaldehydedimethylacetal; phenylacetaldehydeglycerinacetal; 2,4,6-trimethyl-4-phenyl-1,3-dioxane; 4,4a,5,9b -tetrahydroindeno[1,2-d]-m-dioxine; 4,4a,5,9b-tetrahydro-2,4-dimethylindeno[1,2-d]-m-dioxine;

the aromatic and araliphatic aldehydes, with preference here for benzaldehyde; phenylacetaldehyde; 3-phenylpropanal; hydratropaaldehyde; 4-methylbenzaldehyde; 4-methylphenylacetaldehyde; 3-(4-ethylphenyl)-2,2-dimethylpropanal; 2-methyl-3-(4-isopropylphenyl)propanal; 2-methyl-3-(4-tert.-butylphenyl)propanal; 2-methyl-3-(4-isobutylphenyl)propanal; 3-(4-tert.-butylphenyl)propanal; cinnamaldehyde; alpha -butylcinnamaldehyde; alpha-amyl-cinnamaldehyde; alpha-hexylcinnamaldehyde; 3-methyl-5-phenylpentanal; 4-methoxybenzaldehyde; 4-hydroxy-3-methoxybenzaldehyde; 4-hydroxy-3-ethoxybenzaldehyde; 3,4-methylenedioxybenzaldehyde; 3,4-dimethoxybenzaldehyde; 2-methyl-3-(4-methoxyphenyl)propanal; 2-methyl-3-(4-methylenedioxyphenyl)propanal;

the aromatic and araliphatic ketones, with preference here for acetophenone; 4-methylacetophenone; 4-methoxyacetophenone; 4-tert.-butyl-2,6-dimethylacetophenone; 4-phenyl-2-butanone; 4-(4-hydroxyphenyl)-2-butanone; 1-(2-naphthalenyl)ethanone; 2-benzofuranylethanone; (3-methyl-2-benzofuranyl)ethanone; benzophenone; 1,1,2,3,3,6-hexamethyl-5-indanyl methyl ketone; 6-tert.-butyl-1,1-dimethyl-4-indanyl methyl ketone; 1-[2,3-dihydro-1,1,2,6-tetramethyl-3-(1-methylethyl)-1H-5-indenyl]ethanone; 5',6', 7',8'-tetrahydro-3',5',5',6',8',8'-hexamethyl-2-acetonaphthone;

the aromatic and araliphatic carboxylic acids and their esters, with preference here for benzoic acid; phenyl acetic acid; methyl benzoate; ethyl benzoate; hexyl benzoate; methyl phenyl acetate; ethyl phenyl acetate; geranyl phenyl acetate; phenyl ethyl-phenyl acetate; methyl cinnamate; ethyl cinnamate; benzyl cinnamate; phenyl ethyl cinnamate; cinnamyl cinnamate; allyl phenoxy acetate; methyl salicylate; isoamyl salicylate; hexyl salicylate; cyclohexyl salicylate; cis-3-hexenyl salicylate; benzyl salicylate; phenyl ethyl salicylate; methyl 2,4-dihydroxy-3,6-dimethylbenzoate; ethyl 3-phenylglycidate; ethyl 3-methyl-3-phenylglycidate;

the nitrogen-containing aromatic compounds, with preference here for 2,4,6-trinitro-1,3-dimethyl-5-tert.-butylbenzene; 3,5-dinitro-2,6-dimethyl-4-tert.-butylacetophenone; cinnamic acid nitrile; 3-methyl-5-phenyl-2-pentenoic acid nitrile; 3-methyl-5-phenylpentanoic acid nitrile; methyl anthranilate; methyl-N-methyl anthranilate; Schiffs bases of methyl anthranilate with 7-hydroxy-3,7-dimethyloctanal, 2-methyl-3-(4-tert.-butylphenyl)propanal or 2,4-dimethyl-3-cyclohexenecarbaldehyde; 6-isopropylquinoline; 6-isobutylquinoline; 6-sec.-butylquinoline; 2-(3-phenylpropyl)pyridine; indene; scatole; 2-methoxy-3-isopropylpyrazine; 2-isobutyl-3-methoxypyrazine;

the phenols, phenyl ethers and phenyl esters, with preference here for estragole; anethole; eugenol; eugenyl methyl ether; isoeugenol; isoeugenyl methyl ether; thymol; carvacrol; diphenyl ether; beta-naphthyl methyl ether; beta-naphthyl ethyl ether; beta-naphthyl isobutyl ether; 1,4-dimethoxybenzene; eugenyl acetate; 2-methoxy-4-methylphenol; 2-ethoxy-5-(1-propenyl)phenol; p-cresylphenyl acetate;

the heterocyclic compounds, with preference here for 2,5-dimethyl-4-hydroxy-2H-furan-3-one; 2-ethyl-4-hydroxy-5-methyl-2H-furan-3-one; 3-hydroxy-2-methyl-4H-pyran-4-one; 2-ethyl-3-hydroxy-4H-pyran-4-one;

the lactones, with preference here for 1,4-octanolide; 3-methyl-1,4-octanolide; 1,4-nonanolide; 1,4-decanolide; 8-decen-1,4-olide; 1,4-undecanolide; 1,4-dodecanolide; 1,5-decanolide; 1,5-dodecanolide; 4-methyl-1,4-decanolide; 1,15-pentadecanolide; cis- and trans-11-pentadecen-1,15-olide; cis- and trans-12-pentadecen-1,15-olide; 1,16-hexadecanolide; 9-hexadecen-1,16-olide; 10-oxa-1,16-hexadecanolide; 11-oxa-1,16-hexadecanolide; 12-oxa-1,16-hexadecanolide; ethylene-1,13-dodecane dioate; coumarin; 2,3-dihydrocoumarin; octahydrocoumarin.

Preference according to the invention is for a fragrance mixture as described above, wherein (i) the compound of formula (i) or (ii) one, a plurality of or all compounds of formula (I) is or are selected from the group consisting of cyclohexadec-8-en-1-one (Aurelione, CAS No. 88642-03-9, 3100-36-5; Globanone, CAS No. 3100-36-5), cyclohexadecanone (Isomuscone, CAS No. 2550-52-9), oxacyclohexadecen-2-one (Globalide, CAS No. 34902-57-3, 111879-80-2), cyclopentadecanolide (Macrolide, CAS No. 106-02-5) and (9Z)-17-Oxacycloheptadec-9-en-1-one (Ambrettolide, CAS No. 28645-51-4).

Particularly preferred is a fragrance mixture according to the invention, wherein the quantity of compound(s) of formula (I) in the fragrance mixture is sufficient, to mask or decrease the or one or a plurality of unpleasant olfactory impressions of the or one, a plurality of or all the fragrances according to ingredient (B), wherein the or one, a plurality of or all of the unpleasant olfactory impressions is or are preferably selected from among fatty, technical and metallic, and/or to enhance the or one or a plurality of pleasant olfactory impressions of the or one, a plurality of or all fragrances according to ingredient (B), in particular to enhance or improve the natural freshness and/or radiance of the or one, a plurality of or all fragrances according to ingredient (B) and/or to enhance the or a flowery scent of the or one, a plurality of or all fragrances according to ingredient (B), preferably a scent of the jasmine type.

For the purposes of the present invention such a fragrance mixture according to the invention is particularly preferable, wherein the olfactory substance or one, a plurality of or all fragrances according to ingredient (B) is or are selected from the group consisting of methyl dihydrojasmonate, benzyl salicylate, cis-3-hexenyl salicylate, isoamyl salicylate, hexyl salicylate, 2,3,8,8-tetramethyl-1,2,3,4,5,6,7,8-octahydro-2-naphthalenylmethyl ketone, linalyl acetate, ethyllinalyl acetate, cedryl methyl ether, cedryl methyl ketone, cedryl acetate, (4aR,5R,7aS,9R)-octahydro-2,2,5,8,8,9a-hexamethyl-4H-4a,9-methano azuleno (5,6-d)-1,3-dioxol), 1',1',5',5'-tetra methyl-hexahydro-spiro[1.3-dioxolan-2.8'(5'H)-2H-2.4a]methanonaphthalene, cyclododecyl methyl ether, (ethoxymethoxy)cyclododecane, decahydro-beta-naphthyl acetate, 4,7-methano-3a,4,5,6,7,7a-hexahydro-5(-6)-indenyl acetate, allyl-3-cyclohexyl propionate, allylcyclohexyloxy acetate, benzyl benzoate, benzyl cinnamate, 15-hydroxy-Pentadecanonsaurelacton, 3-methyl-cyclopentadecenone, 1,3,4,6,7,8-hexahydro-4,6,6,7,8,8-hexamethyl cyclopenta[g]-2-benzopyrane, 2-[1-(3,3-dimethylcyclohexyl)ethoxy]-2-methyl-, 1-propanoate, 1,4-dioxacycloheptadecan-5,17-dione, 3-methyl-cyclopentadecanone, 3a,6,6,9a-tetramethyl dodecahydronaphtho[2,1-b]furan, alpha-irone, beta-irone, alpha-n-methylionone, beta-n-methylionone, alpha-isomethylionone, beta-isomethylionone and allyl ionone, 2-methyl-3-(4-tert-butylphenyl)propanal, 4-(4-hydroxy-4-methylpentyl)-3-cyclohexencarboxaldehyde, 2-methyl-4-(2,6,6-trimethyl-1-cyclohexen-1-yl)-2-butenal, 1-methyl-4-(4-methyl-3-penten-1-yl)-3-cyclohexencarboxaldehyde, 3-(3-isopropyl-phenyl)-butyraldehyde, (E)-2,6,10-trimethyl-undeca-5,9-dienal, benzo[1,3]dioxole-5-carbaldehyde, 2,2-dimethyl-3-phenyl-propan-1-ol, 2,2-dimethyl-3-m-tolyl-propan-1-ol, 1-(4-isopropyl-cyclohexyl)-ethanol, (4-isopropyl-cyclohexyl)-methanol, 2-phenyl-ethanol, 2-isobutyl-4-methyl-tetrahydro-pyran-4-ol, 3,7-dimethyl-octa-1,6-dien-3-ol, (Z)-3,7-dimethyl-octa-2,6-dien-1-ol, (E)-3,7-dimethyl-octa-2,6-dien-1-ol, 3,7-dimethyl-oct-6-en-1-ol, 2,6-dimethyl-oct-7-en-2-ol, 3,7-dimethyl-octan-1-ol, 2-methyl-6-methylenoct-7-en-2-ol and (E/Z)-3,7-dimethyl-nona-1,6-dien-3-ol.

The proportion of compound(s) of formula (I) in a fragrance mixture according to the invention, in relation to the total weight of the fragrance mixture, is preferably 1 wt. % or less, preferably 0.1 wt. % or less, particularly preferably 0.001 wt. % or less.

A further aspect of the present invention concerns a perfumed product, containing a fragrance mixture according to the invention (as described herein) or one or a plurality of compounds of formula (I), preferably a perfume oil according to the invention (as described above), in a sensorially effective quantity.

Here the proportion of fragrance mixture in relation to the total weight of the product is preferably in the range 0.01 through 10 wt. %, preferably in the range 0.1 through 5 wt. %, particularly preferably in the range 0.25 through 3 wt. %.

For preferred compounds of formula (I) to be used or contained and for any further ingredients of a fragrance mixture contained that stated above applies by analogy.

For the avoidance of doubt, it is stated that (perfumed) products according to the invention in the context of this application are understood to be intentionally created or manufactured products, but not naturally occurring substance mixtures as for example may be obtained by extraction from vegetable starting materials.

Preferred products are, for example, perfume extracts, eaux de parfum, eaux de toilettes, aftershaves, eaux de colognes, pre-shave products, splash colognes and perfumed freshening wipes as well as perfumed or perfuming acidic, alkaline and neutral cleaners, such as for example for floor cleaners, window cleaners, dishwashing detergents, bath and sanitary cleaners, scouring milk, solid and liquid WC cleaners, WC sticks, WC blocks (liquid or solid), pulverulent and foam carpet cleaners, liquid laundry detergents, pulverulent laundry detergents, laundry pretreatment agents, such as bleaches, soaking agents and stain removers, fabric softeners, washing soaps, washing tablets, disinfectants, surface disinfectants, and air fresheners in liquid or gel form or deposited on a solid carrier, in particular for deodorizing air from climate control systems and industrial processes, as well as air fresheners in the form of aerosol or pump sprays, waxes and polishes, such as furniture polishes, floor waxes, shoe creams, reinforcing, impregnating or deodorizing textile treatment agents, diapers, sanitary towels, panty liners, plasters, and body care compositions, such as for example solid and liquid soaps, shower gels, shampoos, shaving soaps, shaving foams, bath oils, cosmetic emulsions of the oil-in-water, water-in-oil and water-in-oil-in-water type, such as for example skin creams and lotions, face creams and lotions, sunscreen creams and lotions, aftersun creams and lotions, hand creams and lotions, foot creams and lotions, depilatory creams and lotions, aftershave creams and lotions, tanning creams and lotions, hair care products, such as for example hairsprays, hair gels, hair setting lotions, hair rinses, permanent and semipermanent hair colorants, hair-shaping compositions, such as cold waves and hair-smoothing compositions, hair tonics, hair creams and lotions, deodorants and antiperspirants, such as for example underarm sprays, roll-ons, deodorant sticks, deodorant creams, products in decorative cosmetics, such as for example for eyeshadows, make-up, lipsticks, mascara, and candles, lamp oils, joss-sticks, animal litter, cat litter, insecticides, repellents, liquid and gaseous propellants, heating oils and heating gases.

Particularly preferred is a product according to the invention selected from the group consisting of perfume extracts, eaux de parfum, eaux de toilettes, aftershaves, eaux de colognes, pre-shave products, splash colognes, perfumed freshening wipes, acidic, alkaline and neutral cleaners, textile fresheners, ironing aids, liquid laundry detergents, pulverulent laundry detergents, laundry pretreatment agents, fabric softeners, washing soaps, washing tablets, disinfectants, surface disinfectants, air fresheners, aerosol sprays, waxes and polishes, body care compositions, hand creams and lotions, foot creams and lotions, depilatory creams and lotions, aftershave creams and lotions, tanning creams and lotions, hair care products, deodorants and antiperspirants, products in decorative cosmetics, candles, lamp oils, joss-sticks, insecticides, repellents and propellants.

A product according to the invention can also form the basis of a product to improve an odor by decreasing an unpleasant odor (in particular as described above) or by enhancing a pleasant olfactory aspect (in particular as described herein).

According to a preferred configuration the compounds of formula (I) to be used according to the invention are adsorbed by a carrier which ensures both a fine distribution of the compounds in the product and also a controlled release of these during application. Such carriers can be porous inorganic materials such as silica gels, zeolites, gypsum, clay, granulated clay and gas concrete and so on, or organic materials such as wood and cellulose-based substances.

The compounds of formula (I) to be used according to the invention or corresponding mixtures of these or fragrance mixtures (as described herein) can also be in microencapsulated, spray-dried, inclusion complex or extrusion product form and in such form can be added to a product.

If necessary the properties of such compounds to be used according to the invention of formula (I) modified in this way can be further optimized through so-called coating with suitable materials for a controlled release of perfume, to which end wax-like synthetic materials such as for example polyvinyl alcohol are preferably used.

Microencapsulation of the compounds to be used according to the invention of formula (I) can for example take place by the so-called coacervation method with the help of capsule materials, for example made from polyurethane-like substances or soft gelatin. Spray-dried compounds of formula (I) can for example be produced by spray drying a substance to be used according to the invention, that is to say an emulsion or dispersion containing the alcohol of the compound of formula (I) or a corresponding mixture, wherein for the carrier substance modified starches, proteins, dextrin and/or vegetable gums can be used. Inclusion complexes for example can be produced by adding dispersions which are or contain compounds to be used according to the invention of formula (I) or corresponding mixtures of these, and cyclodextrins or urea derivatives in a suitable solvent, such as water. Extrusion products can result from the blending of the compound(s) to be used according to the invention of formula (I) or corresponding mixtures with a suitable waxy substance and by extrusion with subsequent solidification, optionally in a suitable solvent, e.g. isopropanol.

The compounds to be used according to the invention of formula (I) or corresponding mixtures can be used in many preparations or products, wherein they are preferably combined with one or a plurality of the following adjuvants or active ingredients:

preservatives, abrasives, antiacne agents, compounds against ageing of the skin, antibacterial agents, anti-cellulitis agents, antidandruff agents, antiphlogistic agents, irritation-preventing agents, anti inflammatory agents, antimicrobial agents, antioxidants, astringents, antiperspirants, antiseptic agents, antistatics, binders, buffers, support materials, chelating agents, cell stimulants, cleansing agents, conditioning agents, depilators, surface-active substances, deodorizing agents, antiperspirants, softeners, emulsifiers, enzymes, ethereal oils, fibers, fixers, foaming agents, foam stabilizers, substances to prevent foaming, foam boosters, fungicides, gelling agents, gel forming agents, hair care products, hair styling agents, hair straightening agents, moisture-donating agents, moisturizing substances, moisture-retaining substances, bleaching agents, (textile) strengthening agents, stain-removing agents, optically brightening agents, impregnating agents, dirt-repellent agents, friction-reducing agents, lubricants, moisturizing crèmes, ointments, opacifying agents, plasticizing agents, covering agents, polish, gloss agents, polymers, powders, proteins, lipid replenishing crèmes, polishing agents, silicones, skin soothing agents, skin cleansing agents, skin care agents, skin repair agents, skin lightening agents, skin-protecting agents, skin-softening agents, skin-cooling agents, skin-warming agents, stabilizers, UV-absorbing agents and UV-filters, detergents, fabric conditioners, suspending agents, skin tanning agents, thickening agents, vitamins, oils, waxes, fats, phospholipids, saturated fatty acids, mono- or polyunsaturated fatty acids, α-hydroxy acids, polyhydroxy-fatty acids, condensers, dyestuffs, color-protecting agents, pigments, anti-corrosive agents, aromas, flavorings, fragrances, polyols, surfactants, electrolytes, organic solvents or silicone derivatives.

According to a configuration of the present invention a preferred product according to the invention, in particular a deodorant or similar, contains (depending on the desired mode of action) additionally one or a plurality of the following active substances:

(1) antimicrobial substances which inhibit the development of the microorganisms responsible for the smell of sweat, for example, Triclosan® (5-chloro-2-(2,4-dichlorophenoxy) phenol), triclocarban, chlorhexidine, chlorhexidine hydrochloride, chlorhexidine diacetate, chlorhexidine digluconate, 2-phenoxyethanol, farnesol, glycerol esters and ethers, such as glycerol monoluarate, glycerol monocaprate, Hexoxyglycerin, octoxyglycerol (=Ethylhexylglycerin, 3-(2-ethylhexyloxy-1,2-propanediol) or Sensiva® SC 50 (of Schuelke & Mayr), aliphatic 1,2-diols such as 1,2-decanediol (EP 1269983), araliphatic alcohols, such as for example described in EP 799 174, preferably 4-methyl-4-phenyl-2-pentanol (Vetikol; WO 03/024 907) or 2-methyl-4-phenyl-2-butanol (1,1-dimethyl-3-phenylpropanol, alpha, alpha -dimethylphenethylcarbinol), I-menthyl methyl ether as described in WO 02/41861, 2-Benzylheptan-1-ol (Jasmol, 2-n-pentyl-3-phenylpropane-1-ol), 2,2-dimethyl-3-phenylpropanol (Muguetalkohol, c.f. U.S. Pat. No. 4,091,090), Antimicrobial active secondary alcohol, such as for example described in WO 2005/004601, in particular 3-methyl-6-phenyl-2-hexanol, 4-(2,4-dimethylphenyl)-2-butanol, 6-(4-isopropylphenyl)-3-methyl-2-hexanol, 4-(2,4 0.5-trimethylphenyl)-2-butanol, 3,3-dimethyl-4-phenyl-2-butanol, 3-methyl-4-(2-methylphenyl)-2-butanol, 6-(3,4-dimethylphenyl)-2-hexanol, aliphatic carboxylic acids such as 2-hexyloctanoic acid, 2-hexyldecanoic acid, 2-butyloctanoic acid, or 2-butyldecanoic acid;

(2) enzyme-inhibiting substances which prevent the action of enzymes that are involved in the formation of sweat odor, for example citric acid esters and metal-chelating agents such as EDTA (ethylenediaminetetraacetic acid), EGTA [ethylene bis(oxyethylenenitrilo)tetraacetic acid], and DTPA (diethylenetriaminepentaacetic acid, pentetic acid);

(3) odor-absorbing substances that absorb substances responsible for the odor, for example, zinc ricinoleate, cyclodextrins;

(4) antiperspirants that inhibit perspiration and thus deprive the bacteria responsible for body odor of a breeding ground. Aastringent metal salts are preferably generally used as antiperspirants, particularly inorganic and organic metal salts of the elements aluminum, zinc, magnesium, tin and zirconium, and mixtures thereof, wherein in particular halides such as aluminum chloride, basic aluminum hydroxychlorides, zirconyl oxychloride and zirconyl hydroxychloride and mixtures thereof may be used. Often these aluminum and zirconium salts and mixtures thereof are also used in a complexed form, wherein the complexing agents used are preferably propylene glycol, polyethylene glycol or glycine.

The present invention also concerns a method for producing a perfumed product, in particular a perfumed product according to the invention (as described herein), comprising the following steps:

i) provision of the ingredients (A) and (B) as defined above, preferably provision of a fragrance mixture according to the invention as described above, in particular a fragrance mixture according to the invention as indicated herein as preferred, ii) provision of one or a plurality of further ingredients of the perfumed product to be produced, and iii) bringing into contact or mixing the further ingredients provided in step ii) with a sensorially effective quantity of the ingredients (A) and (B) provided in step i) or the fragrance mixture provided in step i).

For the ingredients (A) and (B) and the further ingredients of the product to be produced that stated above applies by analogy.

The present invention further concerns a method for masking or decreasing the or one or a plurality of unpleasant olfactory impressions of one or a plurality of substances with an unpleasant odor, wherein the substance(s) is or are not a compound(s) of formula (I)

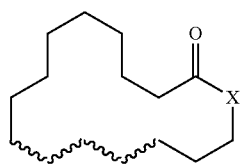

(I)

wherein it is the case that:
none, one or two of the four jagged lines denotes or denote a double bond and the other jagged lines in each case denote a single bond, and
X is selected from —O—, —CH$_2$— and —O—CH$_2$—, comprising the following step:
mixing the substance(s) with an unpleasant odor not corresponding to formula (I) with (i) an individual compound of formula (I) or (ii) a mixture comprising or consisting of two or a plurality of compounds of formula (I), wherein the quantity of compound(s) of formula (I) is sufficient to decrease or mask the unpleasant olfactory impression(s) of the substance(s) with an unpleasant odor.

A further aspect of the present invention concerns a method for enhancing the or one or a plurality of pleasant olfactory impressions of one or a plurality of substances with a pleasant odor, in particular for enhancing or improving the natural freshness and/or radiance of one or a plurality of substances with a pleasant odor and/or for enhancing the or a flowery scent of one or a plurality of substances with a pleasant odor, preferably a scent of the jasmine type, wherein the substance(s) is or are not a compound of formula (I)

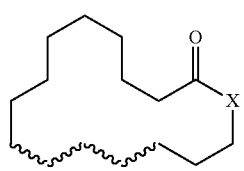

(I)

wherein it is the case that:
none, one or two of the four jagged lines denotes or denote a double bond and the other jagged lines in each case denote a single bond, and
X is selected from —O—, —CH$_2$— and —O—CH$_2$—, comprising the following step:
mixing the substance(s) with a pleasant odor not corresponding to formula (I) with (i) an individual compound of formula (I) or (ii) a mixture comprising or consisting of two or a plurality of compounds of formula (I), wherein the quantity of compound(s) of formula (I) is sufficient, to enhance the pleasant olfactory impression(s) of the substance(s) with a pleasant odor or to enhance or improve the natural freshness and/or radiance.

With the method according to the invention described above, for the compounds to be used of formula (I) or mixtures of these and the (olfactory) substance(s) not corresponding to formula (I), the scents to be enhanced or masked and the preferred quantities or ratios, that stated above applies by analogy.

In this connection a method is also relevant with which it can be assessed whether a certain substance (substance or mixture) is a suitable substance for a particular task, that is to say whether by using this substance an unpleasant odor within the meaning of the present invention can be masked or decreased and/or a pleasant olfactory impression enhanced.

In the context of the present invention, in order to test the suitability of a test substance (comprising or consisting of one or a plurality of compounds of formula (I)) for masking or decreasing an unpleasant odor a method is preferably used, that comprises the following steps:

a) producing or providing a (malodorous) standard mixture (standard mixture with an unpleasant odor) comprising or consisting of a substance (substance or mixture) with an unpleasant odor, b) producing or providing a test mixture similarly comprising the substance with an unpleasant odor and also the test substance under investigation, and c) comparing the (malodorous) impressions of the (malodorous) standard mixture and the test mixture.

Such a method can in a similar manner be used for testing the suitability of a test substance (comprising or consisting of one or a plurality of compounds of formula (I)) for enhancing a pleasant olfactory impression.

A test method as described above is preferably performed at a temperature of 20° C. and a pressure of 1013 mbar.

The test method is preferably carried out in such a way that the concentrations of the substance with an unpleasant (or pleasant) odor in the (malodorous) standard mixture and the test mixture are equal. This allows a particularly good comparison of the two mixtures.

The (malodorous) impressions of the (malodorous) standard mixture and the test mixture and preferably also the perfume or scent intensity of these mixtures is preferably assessed by each of 8 or a plurality of testers (experts) by smelling these in comparison with one another. By way of example, a malodorous standard mixture is assigned an intensity of 6 here.

The testers are selected on the basis of their ability to reproducibly assess the strength of odors and prior to the series of tests trained to recognize the unpleasant or pleasant odors (to be reduced or enhanced).

In the following the invention is explained in more detail using selected examples. The examples serve to clarify the invention, without restricting the range of protection of the claims. Percentages refer to the weight, unless otherwise indicated.

EXAMPLE 1

Odor Description of Selected Fragrances Following Addition of Selected Compounds of Formula (I)

| Fragrance | Compound of formula (I) | Mass ratio of fragrance:Compound of formula (I) | Odor description in comparison with the odor of the pure fragrance |
|---|---|---|---|
| Mugetanol (M = 170 g/mol) | a) Globanone, CAS No. 3100-36-5 b) Globalide, CAS No. 34902-57-3 | a) 100:0.5 b) 100:0.1 | softer, more natural, more flowery, less technical |
| Dihydromyrcenol (M = 156 g/mol) | a) Globalide, CAS No. 34902-57-3 b) Globanone, CAS No. 3100-36-5 | a) 100:0.1 b) 100:0.2 | less technical, more naturally lavender-like, more flowery |
| Linalool (M = 154 g/mol) | Isomuscone, CAS No. 2550-52-9 | 100:0.1 | less technical, fresher, more natural |
| Geraniol (M = 154 g/mol) | Globalide, CAS No. 34902-57-3 | 100:0.1 | less fatty, less metallic, rounder, more natural, more volume |
| Citronellol (M = 156 g/mol) | a) Globalide, CAS No. 34902-57-3 b) Globanone, CAS No. 3100-36-5 | a) 100:0.05 b) 100:0.1 | less fatty, more natural, rosier |
| Phenoxanol (M = 178 g/mol) | a) Globalide, CAS No. 34902-57-3 b) Globanone, CAS No. 3100-36-5 | a) 100:0.1 b) 100:0.2 | less technical, more rosy, more natural |
| Lilial ® (M = 204 g/mol) | Globalide, CAS No. 34902-57-3 | 100:0.1 | less technical, fresher, more natural, stronger smelling of lily of the valley |
| Aldehyde MNA (M = 184 g/mol) | Globalide, CAS No. 34902-57-3 | 100:0.1 | less fatty, less metallic, rounder |
| Melonal ® (M = 140 g/mol) | Ambrettolide, CAS No. 28645-51-4 | 100:0.1 | less technical, less metallic, rounder, more natural |
| Para tert.-butyl-cyclohexanone (M = 154 g/mol) | Globanone, CAS No. 3100-36-5 | 100:0.1 | less technical, rounder, more harmonic, smelling more of patchouli oil, fresher |
| Oryclon ® (M = 198 g/mol) | Globalide, CAS No. 34902-57-3 | 100:0.1 | less technical, rounder, more harmonic, fresher |
| Mayol | Isomuscone, CAS No. 2550-52-9 | 100:0.1 | less technical, less animal-like, rounder, more harmonic, fresher |
| Citronallal | Globalide, CAS No. 34902-57-3 | 100:0.1 | less technically metallic, rosier, more natural |
| Majantol | Macrolide, CAS No. 106-02-5 | 100:0.1 | less technical, rounder, more harmonic, fresher |
| Aldehyde C14 | Globanone, CAS No. 3100-36-5 | 100:0.1 | less technical, rounder, more harmonic, more flowery |
| Ligustral ® | a) Macrolide, CAS No. 106-02-5 b) Globanone, CAS No. 3100-36-5 | a) 100:0.05 b) 100:0.1 | less technical, rounder, more harmonic, more volume |
| Agrumex ® | a) Globalide, CAS No. 34902-57-3 b) Globanone, CAS No. 3100-36-5 | a) 100:0.05 b) 100:0.1 | less technical, rounder, more natural, fruitier |

The olfactory effects described in the description and in the above table of the compounds of formula (I) compared with (other) fragrances were also taken into account in the application examples described below.

EXAMPLE 2

Application Examples

For the formulations described below one of the following perfume oils (according to the invention) can be used as desired:

Perfume Oil P1:

| | |
|---|---|
| Aldehyde C 12 lauric | 3.5 |
| Decenol-9 | 0.5 |
| Vertocitral | 75 |
| Dihydro myrcenol | 170.0 |
| Citronitril | 0.6 |
| Orange oil terpene | 30.0 |
| Eucalyptol | 10.0 |
| Mugwort oil | 1.5 |
| Camphor DL | 10.0 |
| Aldehyde C 14, so-called. | 4.5 |

| | |
|---|---|
| Benzophenone | 10.0 |
| Benzyl acetate | 25.0 |
| Hexyl cinammic aldehyde alpha | 10.00 |
| Agrumex HC | 350.0 |
| Oryclon HC | 100.0 |
| Herbaflorate | 45.0 |
| Herbyl propionate | 75.0 |
| Dipropylene glycol | 146.9 |
| | 1,000.00 |

With the addition of 0.5 parts of Globalide, CAS No. 34902-57-3, (to obtain a perfume oil according to the invention) the mixture is rounder, more harmonic, more natural, stronger and no longer so technical.

With the addition of 1 part Globanone, CAS No. 3100-36-5, (to obtain a perfume oil according to the invention) the mixture has a stronger top note and also gives off a flowery note.

Perfume Oil P2:

| | |
|---|---|
| Undecavertol | 2.5 |
| Dimethyl benzyl carbinyl acetate | 35.0 |
| Agrumex Hydrocarbons | 200.0 |
| Hexenyl acetate cis-3 | 7.5 |
| Vertocitral | 15.0 |
| Oxanthia 50% in TEC | 3.5 |
| Gamma-decalactone | 150.0 |
| Aldehyde C18 so-called | 35.0 |
| Aldehyde C14 so-called | 350.0 |
| Thiomenthanon-8,3 0.1% in DPG | 3.5 |
| Orange oil Bras. | 75.0 |
| Hedione | 100.0 |
| Ethyl methyl butyrate-2 | 1.5 |
| Benzyl acetate | 20.0 |
| Alpha-damascone | 1.5 |
| | 1,000.00 |

With the addition of 0.2 parts of Macrolide, CAS No. 106-02-5, (to obtain a perfume oil according to the invention) the mixture is rounder and no longer so technical, fresher.

With the addition of 0.5 parts of Globalide, CAS No. 34902-57-3, (to obtain a perfume oil according to the invention) the mixture has a more harmonic, more flowery and stronger effect in the direction of jasmine.

Perfume Oil P3:

| | |
|---|---|
| Aceto acetic acid ethyl ester | 40.0 |
| Hexenol cis-3 | 2.0 |
| Terpinyl acetate | 10.0 |
| Fir Balsam abs. 10% in BB | 5.0 |
| Jasmine prunate | 50.0 |
| Ethyl isovalerianate | 6.8 |
| Isoamyl isovalerianate | 1.4 |
| Ethyl caprylate | 6.0 |
| Ethyl caprinate | 4.0 |
| Aldehyde C14 so-called | 50.0 |
| Aldehyde C18 so-called | 3.4 |
| Aldehyde C16 so-called | 40.0 |
| Frambinon ® | 50.0 |
| Ethyl maltol | 20.0 |
| Linalool | 300.0 |
| Dimethyl benzyl carbinyl butyrate | 10.0 |
| Phennirat ® | 60.0 |
| Geranyl butyrate | 10.0 |
| Alpha-damascone | 0.5 |
| Benzyl acetate | 60.0 |
| Gamma-iraldein | 50.0 |
| Anisyl acetate | 10.0 |
| Vanillin | 40.0 |
| Benzaldehyde | 30.0 |
| Agrumex LC | 40.0 |
| Dipropylene glycol | 100.9 |
| | 1,000.00 |

With the addition of 0.5 parts of Globalide, CAS No. 34902-57-3, (to obtain a perfume oil according to the invention) the mixture is rounder, no longer so technical and more natural.

With the addition of 1 part of Isomuscone, CAS No. 2550-52-9, (to obtain a perfume oil according to the invention) the mixture has a more flowery and more harmonic effect.

Perfume Oil P4:

| | |
|---|---|
| Aldehyde C10 | 60.0 |
| Aldehyde C11 MOA | 5.0 |
| Florazon | 5.0 |
| Ozonil | 1.0 |
| Scentenal | 3.0 |
| Vertocitral | 3.0 |
| Vertosine | 1.0 |
| Dynascone mixture 1:1 10% in DPG | 2.0 |
| Mintonat | 25.0 |
| Dihydromyrcenol | 150.0 |
| Terpinyl acetate | 50.0 |
| Litsea cubebaoel | 50 |
| Agrunitril | 6.0 |
| Citrowanil ® B | 5.0 |
| Citronellal | 3.0 |
| Citrylal | 11.0 |
| Nerolione | 1.0 |
| Lavandin grosso oil | 2.0 |
| *Eucalyptus globulus* oil | 5.0 |
| Menthol rac. | 120.0 |
| Spearmint oil | 2.0 |
| Herboxane | 8.0 |
| Thymol | 4.0 |
| Pineoel | 200.0 |
| Isobornyl acetate | 110.0 |
| Aldehyde C14 so-called | 3.0 |
| Cyclamen aldehyde | 1.0 |
| Tetrahydrolinalool | 1.0 |
| Terpineol | 10.0 |
| Phenyl ethyl acetate | 2.0 |
| Citronellol | 10.0 |
| Diphenyl oxide | 10.0 |
| Benzyl acetate | 10.0 |
| Methyl benzoate | 2.0 |
| Hexyl salicylate | 100.0 |
| Beta-ionone | 1.0 |
| Heliotropin | 3.0 |
| Agrumex HC | 25.0 |
| Orylclon | 310.0 |
| Herbaflorate | 38.0 |
| Koavone | 10.0 |
| Ambrocenide ® 10% in DPGl | 2.0 |
| BHT Jonol | 25.0 |
| Dipropylene glycol | 250.0 |
| | 1,000.0 |

With the addition of 0.5 parts of Globalide, CAS No. 34902-57-3, (to obtain a perfume oil according to the invention) the mixture is rounder, more flowery, no longer so technical.

With the addition of 1 part Ambrettolide, CAS No. 28645-51-4, (to obtain a perfume oil according to the invention) the mixture no longer smells so technical and achieves more volume.

Perfume Oil P5:

| | |
|---|---|
| Vertocitral | 1.0 |
| Galbanum essence | 3.0 |
| Allly amyl glycolate ® | 5.0 |
| Cyclogalbanate ® | 10.0 |
| Bergamot Identoil ® colorless | 100.0 |
| Dihydrmyrcenol | 200.0 |
| Terpinyl acetate | 100.0 |
| Citral | 10.0 |
| Geranylnitril Replacer | 3.0 |
| Petigrain oil | 10.0 |
| Methyl naphthyl ketone | 5.0 |
| Lavandin grosso | 30.0 |
| Rosemary oil | 10.0 |
| Peppermint oil Arv, DMO | 5.0 |
| Fir Balsam abs. 10% DPG | 1.0 |
| Pine needle abs. | 0.6 |
| Hexyl acetate | 1.0 |
| Delta-decalactone 1% DEP | 0.5 |
| Maltol 1% DPG | 10.0 |
| Calone 1951 0.1% DPG | 0.5 |
| Hydroxycitronellal | 25.0 |
| *Geranium* oil | 5.0 |
| Citronellol | 10.0 |
| Alpha-damascone | 2.0 |
| Hedione | 10.0 |
| Alpha-hexylcinnameldehyde | 44.0 |
| Boronal 10% DPG | 1.0 |
| Isoraldein 70 | 10.1 |
| Oryclon HC | 17.5 |
| Oryclon special | 32.5 |
| Cedar wood oil 10% DPG | 2.0 |
| Caryophyllene acetate | 17.6 |
| Vertofix 10% DPG | 2.0 |
| Cedryl acetate | 2.1 |
| Palisandal | 35.0 |
| Vetiver oil 10% DPG | 1.0 |
| Sandalwood oil mixture 1 10% DPG | 2.0 |
| Isobornyl cyclohexanol | 4.2 |
| Evernyl | 2.1 |
| Mousse C abs. 70A757 | 1.0 |
| Ambrinol S 10% DPG | 2.0 |
| Ambroxide 10% IPM | 2.0 |
| Ketamber 10% TEC | 2.0 |
| Hercolyn D-E | 34.2 |
| Dipropylene glycol | 228.1 |
| | 1,000.0 |

With the addition of 0.5 g von Globalide, CAS No. 34902-57-3, (to obtain a perfume oil according to the invention) the mixture is rounder, not so technical, fresher and natural.

With the addition of 1 g von Globanone, CAS No. 3100-36-5, (to obtain a perfume oil according to the invention) the mixture achieves more volume and has a more natural effect.

EXAMPLE F1

Washing Powder

| Material | Chemical name | Function | wt. % | wt. % |
|---|---|---|---|---|
| Sodium metasilicate pentahydrate | Sodium metasilicate pentahydrate | | To 100 | To 100 |
| Sodium hydrogen carbonate | Sodium hydrogen carbonate | Alkali | 15.0 | 15.0 |
| Sodium percarbonate | Sodium carbonate peroxyhydrate | Bleaching agent | 15.0 | 15.0 |
| Peractive AC Blue | TAED/Na-Carboxymethylcellulose | Activator | 5.00 | 5.00 |
| Genapol OA-080 | Oxoalkohol C14-15, 8EO | Non-ionic surfactant | 3.00 | 3.00 |
| Texapon K12 powder | Sodium Lauryl Sulphate C12 | Anionic surfactant | 7.00 | 7.00 |
| Tinopal CBS-X | | Brightener | 0.50 | 0.50 |
| Savinase 6.0 T, Type W | Protease | Enzyme | 0.40 | 0.40 |
| Termamyl 120 T | Alpha-Amylase | Enzyme | 0.30 | 0.30 |
| Sodium sulfate | Sodium Sulphate | Filler | 5.50 | 5.50 |
| Perfume oil according to P1, P2, P3, P4 or P5 | | Parfum (Fragrance) | 0.30 | 0.50 |

EXAMPLE F2

All-Purpose Cleaner

| Material | Chemical name | Function | wt. % | wt. % |
|---|---|---|---|---|
| Deionized water | Water | Solvent | To 100 | To 100 |
| Mergal K9N | 5-Chloro-2-methyl-3-(2H)-isothiazolone and 2-methyl-3-(2H)-isothiazolone | Preservative | 0.1 | 0.1 |
| Tri sodium citrate dihydrate | Tri Sodium Citrate Dihydrate | Complexing agent | 3.0 | 3.0 |
| Zetesol NL-2 | Fatty alcohol C12-14-sulfate, Sodium | Anionic surfactant | 30.0 | 30.0 |
| Imbentin C/125/055 | Fatty alcohol C12-C15, 8EO | Non-ionic surfactant | 5.0 | 5.0 |
| Ethanol | Ethanol | Solvent | 2.0 | 2.0 |
| Perfume oil according to P1, P2, P3, P4 or P5 | | Parfum (Fragrance) | 0.3 | 0.5 |

EXAMPLE F3

Shampoo

| Material | INCI-Name | wt. % | wt. % |
|---|---|---|---|
| Deionized water | Water | To 100 | To 100 |
| Plantacare PS 10 | Sodium Laureth Sulfate, Lauryl Glucoside | 20.0 | 20.0 |
| Euperlan PK 771 | Glycol Distearate, Sodium Lauryl Sulfate, Cocamide MEA, Laureth-10 | 6.0 | 6.0 |
| Dragocid Liquid | Phenoxyethanol, Methylparaben, Ethylparaben, Butylparaben, Propylparaben, Isobutylparaben | 0.5 | 0.5 |
| Sodium chloride | Sodium Chloride | 1.4 | 1.4 |
| Citric acid monohydrate crystalline | Citric Acid | 0.1 | 0.1 |
| Perfume oil according to P1, P2, P3, P4 or P5 | Parfum (Fragrance) | 0.5 | 0.8 |

EXAMPLE F4

Shower Gel

| Material | INCI-Name | wt. % | wt. % |
|---|---|---|---|
| Deionized water | Water | To 100 | To 100 |
| Plantacare PS 10 | Sodium Laureth Sulfate, Lauryl Glucoside | 20.0 | 20.0 |
| Dragocid Liquid | Phenoxyethanol, Methylparaben, Ethylparaben, Butylparaben, Propylparaben, Isobutylparaben | 0.5 | 0.5 |
| Sodium chloride | Sodium Chloride | 1.4 | 1.4 |
| Citric acid monohydrate crystalline | Citric Acid | 1.3 | 1.3 |
| Perfume oil according to P1, P2, P3, P4 or P5 | Parfum (Fragrance) | 0.5 | 0.7 |

EXAMPLE F5

Fabric Softener

| Material | Chemical name | Function | wt. % | wt. % |
|---|---|---|---|---|
| Deionized water | Water | Solvent | To 100 | To 100 |
| Rewoquat WE 18 | Dialkylesterammonium-ethosulfate | Cationic surfactant | 16.6 | 16.6 |
| Mergal K9N | 5-Chloro-2-methyl-3-(2H)-isothiazolone and 2-methyl-3-(2H)-isothiazolone | Preservative | 0.10 | 0.10 |
| Dow Corning 1520 Antifoam | Polydimethyl-siloxane | Defoaming agent | 0.30 | 0.30 |
| Magnesium chloride 1% solution | Magnesium chloride solution | Consistency regulator | 10.00 | 10.00 |
| Perfume oil according to P1, P2, P3, P4 or P5 | | Fragrance | 0.55 | 0.75 |

EXAMPLE F6

Eau De Cologne/Eau De Toilette

| Ingredients | wt. % | wt. % |
|---|---|---|
| Perfume oil according to P1, P2, P3, P4 or P5 | 5 | 10 |
| Ethanol | To 100 | To 100 |
| Water | 18 | 10 |

EXAMPLE F7

Aerosol Pump Spray

| Ingredients | wt. % | wt. % |
|---|---|---|
| Perfume oil according to P1, P2, P3, P4 or P5 | 1.0 | 1.5 |
| Ethanol | To 100 | To 100 |
| Water | 5.0 | 8.0 |
| Alpha-tocopherol | 0.20 | 0.20 |
| Hydroxypropylcellulose | 0.20 | — |
| Rosemary extract soluble in ethanol | 0.22 | — |
| Cetyl alcohol | 1.00 | 0.50 |

EXAMPLE F8

Shampoo

| Ingredients | wt. % | wt. % | wt. % |
|---|---|---|---|
| Sodium lauryl ether sulfate (e.g. Texapon NSO, from Cognis Deutschland GmbH) | 12 | 12 | 12 |
| Cocamidopropyl betaine (e.g. Dehyton K, from Cognis Deutschland GmbH) | 2 | 2 | 2 |
| Sodium chloride | 1.4 | 1.4 | 1.4 |
| Citric acid | 1.3 | 1.3 | 1.3 |
| Phenoxy ethanol, methyl-, ethyl-, butyl- and propylparaben | 0.5 | 0.5 | 0.5 |
| Perfume oil according to P1, P2, P3, P4 or P5 | 0.3 | 0.5 | 0.7 |
| Water | To 100 | To 100 | To 100 |

EXAMPLE F9

Washing Powder

| Ingredients | wt. % | wt. % | wt. % |
|---|---|---|---|
| Linear Na-alkyl benzene sulfonate | 8.8 | 8.8 | 8.8 |
| Ethoxylated fatty alcohol C12-18 (7 EO) | 4.7 | 4.7 | 4.7 |
| Na-soap | 3.2 | 3.2 | 3.2 |
| Defoaming agent DOW CORNING(R) 2-4248S POWDERED ANTIFOAM, silicon oil on zeolites as a carrier material | 3.9 | 3.9 | 3.9 |
| Zeolite 4A | To 100 | To 100 | To 100 |
| Na-carbonate | 11.6 | 11.6 | 11.6 |
| Na-salt of a copolymer of acrylic and maleic acid (Sokalan CP5) | 2.4 | 2.4 | 2.4 |
| Na-silicate | 3.0 | 3.0 | 3.0 |
| Carboxymethylcellulose | 1.2 | 1.2 | 1.2 |
| Dequest 2066([[(Phosphonomethyl)imino]bis[(ethylennitrilo)bis(methylen)]]tetrakis-phosphonic acid, sodium salt) | 2.8 | 2.8 | 2.8 |
| Optical brightener | 0.2 | 0.2 | 0.2 |
| Na-sulfate | 6.5 | 6.5 | 6.5 |
| Protease | 0.4 | 0.4 | 0.4 |
| Sodium perborate tetrahydrate | 21.7 | 21.7 | 21.7 |
| Perfume oil according to P1, P2, P3, P4 or P5 | 0.25 | 0.35 | 0.5 |
| EDTA | 1.0 | 1.0 | 1.0 |

EXAMPLE F10

Liquid Laundry Detergent

| Ingredients | wt. % |
|---|---|
| Deionized water | 39.9 |
| Optical brightener | 0.10 |
| Coconut fatty acids (C12-C18) | 7.5 |
| Potassium hydroxide 50% solution | 4.3 |
| Propane-1,2-diol | 5.00 |
| Fatty alcohols C12-C15, 8 EO | 12.0 |
| Na-salt of secondary alkyl sulfonate (C13-C17) | 17.0 |
| Triethanolamine | 2.0 |
| Trisodium dehydrate | 5.0 |
| Dequest 2066([[(Phosphonomethyl)imino]bis[(ethylennitrilo)bis(methylen)]]tetrakis-phosphonic acid, sodium salt) | 3.0 |
| Ethanol | 3.0 |
| Enzyme | 0.7 |
| Perfume oil according to P1, P2, P3, P4 or P5 | 0.5 |

EXAMPLE F11

Liquid Laundry Detergent Concentrate

| Ingredients | wt. % |
|---|---|
| Deionized water | 13.4 |
| Coconut fatty acids (C12-C18) | 10.0 |
| Fatty alcohols C12-C15, 8 EO | 26.0 |

| Ingredients | wt. % |
|---|---|
| Na-salt of secondary alkyl sulfonate (C13-C17) | 26.5 |
| Triethanolamine | 8.5 |
| Na-salt of fatty alcohol sulfates C12-C14 | 3.0 |
| Ethanol | 5.5 |
| Urea | 4.5 |
| Enzyme | 0.9 |
| Citric acid | 1.0 |
| Perfume oil according to P1, P2, P3, P4 or P5 | 0.7 |

What is claimed is:

1. A method
    (a) for masking or decreasing one or a plurality of unpleasant olfactory impressions of one or a plurality of substances with an unpleasant odor having one or a plurality of the unpleasant olfactory impressions selected from fatty, technical and metallic, and/or
    (b) for enhancing or improving the natural freshness and/or radiance one or a plurality of substances with a pleasant odor and/or for enhancing the flowery scent of one or a plurality of substances with a pleasant odor,
    comprising the step of:
    mixing said substance(s) with an unpleasant odor having one or a plurality of the unpleasant olfactory impressions selected from fatty, technical and metallic, and/or the substance(s) with a pleasant odor with (i) an individual compound of formula (I) or (ii) a mixture comprising or consisting of two or a plurality of compounds of formula (I)

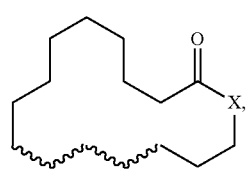

(I)

wherein for the compound of formula (I) or for each compound of formula (I)
    none, one or two of the four jagged lines denotes or denote a double bond and the other jagged lines in each case denote a single bond and
    X is selected from the —O—CH$_2$— and —O—CH$_2$;

wherein said substance(s) with an unpleasant odor and said substance(s) with apleasant odor are not a compound of formula (I), and the ratio of the total mass of the substances with a pleasant and/or unpleasant odor not corresponding to formula (I) to the total mass of compound(s) of formula (I) is greater than or equal to 99:1.

2. The method according to claim 1, wherein
(i) the compound of formula (I) or (ii) one or a plurality of compounds of formula (I) is or are selected from the group consisting of cyclohexadec-8-en-1-one (Aurelione, CAS No. 88642-03-9, 3100-36-5; Globanone, CAS No. 3100-36-5), cyclohexadecanone (Isomuscone, CAS No. 2550-52-9), oxacyclohexadec-2-one (Globalide, CAS No. 34902-57-3, 111879-80-2), cyclopentadecanolide (Macrolide, CAS No. 106-02-5) and (9Z-17-Oxacycloheptadec-9-en-1-one (Ambrettolide, CAS No. 28645-51-4).

3. The method according to claim 1, wherein one or a plurality of the substances(s) with a pleasant and/or unpleasant odor not corresponding to formula (I) is or are selected from the group consisting of fragrances with a molecular weight in the range 150 g/mol through 285 g/mol.

4. The method according to claim 1, wherein one or a plurality of the substance(s) with a pleasant and/or unpleasant odor not corresponding to formula (I) is or are selected from the group consisting of methyl dihydrojasmonate, benzyl salicylate, cis-3-hexenyl salicylate, isoamyl salicylate, hexyl salicylate, 2,3,8,8-tetramethyl-1,2,3,4,5,6,7,8-octahydro-2-napbthalenylmethyl ketone, linalyl acetate, ethyllinalyl acetate, cedryl methyl ether, cedryl methyl ketone, cedryl acetate, (4aR,5R,7aS,9R) -octahydro-2,2,5,8,8,9a-hexamethyl-4H-4a,9-methano azuleno (5,6-d)-1,3-dioxol), 1',1',5',5'-tetra methylhexahydro-spiro[1.3-dioxolan-2.8'(5'H)-2H-2.4a]methanonaphthalene, cyclododecyl methyl ether, (ethoxymethoxy)cyclododecane, decahydro-beta-naphthyl acetate, 4,7-methano-3a,4,5,6,7,7a-hexahydro-5(-6)-indenyl acetate, allyl-3-cyclohexyl propionate, allylcyclohexyloxy acetate, benzyl benzoate, benzyl cinnamate, 15-hydroxy-Pentadocanonsaurelacton, 3-methyl-cyclopentadecenone, 1,3,4,6,7,8-hexahydro-4,6,6,7,8,8-hexamethyl cyclopenta[g]-2-benzopyrane, 2-[1-(3,3-dimethylcyclohexyl)ethoxy]-2-methyl-, 1-propanoate, 1,4-dioxacycloheptadecan-5,17-dione, 3-methyl-cyclopentadecanone, 3a,6,6,9a-tetramethyl dodecahydronaphtho[2,1-b]furan alpha-irone, beta-irone, alpha-n-methylionone, beta-n-methylionone, alpha -isomethylionone, beta-isomethylionone and allyl ionone, 2-methyl-3-(4-tert-butylphenyl)propanal, 4-(4-hydroxy-4-methylpentyl)-3-cyclohexencarboxaldehyde, 2-methyl-4-(2,6,6-trimethyl-1-cyclohexen-1-yl)-2-butenal, 1-methyl-4-(4-methyl-3-penten-1-yl)-3-cyclohexencarboxaldehyde, 3-(3-isopropyl-phenyl)-butyraldehyde, (E)-2,6,10-trimethyl-undeca-5,9-dienal, benzo[1,3]dioxole-5-carbaldehyde, 2,2-dimethyl-3-phenyl -propan-1-ol, 2,2-dimethyl-3-m-tolyl-propan-1-ol, 1-(4-isopropyl-cyclohexyl)-ethanol, (4-isopropyl-cyclohexyl)-methanol, 2-phenyl-ethanol, 2-isobutyl-4-methyl-tetrahydro-pyran-4-ol, 3,7-dimethyl-octa-1,6-dien-3-ol, (Z)-3,7-dimethyl-octa-2,6-dien-1ol, (E)-3,7-dimethyl-octa-2,6-dien-1-ol, 3,7-dimethyl-oct-6-en-1-ol, 2,6-dimethyl-oct-7-en-2-ol, 3,7-dimethyl-octan-1-ol, 2-methyl-6-methylenoct-7-en-2-ol and (E/Z)-3,7-dimethyl-nona-1,6-dien-3-ol.

5. The method according to claim 1, wherein
the quantity of compounds(s) of formula (I) used for decreasing or masking and/or for enhancing is not sufficient to impart a musk odor.

6. A fragrance mixture comprising
(A) (i) an individual compound of formula (I) or
(ii) a mixture comprising or consisting of two or a plurality of compounds of formula (I)

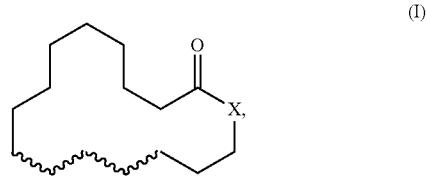

wherein for the compound of formula (I) or for each compound of formula (I)
none, one or two of the four jagged lines denotes or denote a double bond and the other jagged lines in each case denote a single bond and
X is selected from the —O—, and —O—CH$_2$—; and
(B) one, two, three, four, five, six or a plurality of (further) fragrances, wherein the (further) fragrance(s) is or are not a compound of formula (I) and
one, two, three, four, five, six or a plurality of or all of the (further) fragrances has or have a molecular weight in the range 150 g/mol through 285 g/mol, characterized in that the ratio of the total mass of fragrances not corresponding to formula (I) to the total mass of compound(s) of formula (I) is greater than or equal to 99:1,
wherein the quantity of compound(s) of formula (I) in the fragrance mixture is sufficient,
(a) to mask or decrease one or a plurality of unpleasant olfactory impressions of one or a plurality of fragrances according to ingredient (B),
wherein one or a plurality of the unpleasant olfactory impressions is or are selected from fatty, technical and metallic, and/or
(b) to enhance or improve the natural freshness and/or radiance of one or a plurality of fragrances according to ingredient (B) and/or to enhance the flowery scent of one or a plurality of fragrances according to ingredient (B).

7. The fragrance mixture as claimed in claim 6, wherein (i) the compound of formula (I) or (ii) one or a plurality of compounds of formula (I) is or are selected from the group consisting of cyclohexadec-8-en-1-one (Aurelione, CAS No. 88642-03-9, 3100-36-5; Globanone, CAS No. 3100-36-5), cyclohexadecanone (Isomuseone, CAS No. 2550-52-9), oxacyclohexadecen-2-one (Cilobalide, CAS No. 34902-57-3, 111879-80-2), cyclopentadecanolide (Macrolide, CAS No. 106-02-5) and (9Z)-17-Oxacycloheptadec-9-en-1-one (Am-brettolide, CAS No. 28645-51-4).

8. The fragrance mixture according to claim 6, wherein the fragrance or a plurality of fragrances according to ingredient (B) is or are selected from the group consisting of methyl dihydrojasmonate, benzyl salicylate, cis-3-hexenyl salicylate, isoamyl salicylate, hexyl salicylate, 2,3,8,8-tetramethyl-1,2,3,4,5,6,7,8-octahydro-2-naphthalenylmethyl ketone, linalyl acetate, ethyl linalyl acetate, cedryl methyl ether, cedryl methyl ketone, cedryl acetate, (4aR,5R,7aS,9R)-oetahydro-2,2,5,8,8,9a-hexamethyl-4H-4a,9-methano azuleno 5,6-d)-1',1',1',5',5'-tetra methyl-hexahydro-spiro[1.3-dioxolan-2.8'(5'H)-2H-2.4a]methanonaphthalene, cyclododecyl methyl ether, (ethoxymethoxy)cyclododecane, decahydro-beta-naphthyl acetate, 4,7-methano-3a,4,5,6,7,7a-hexahydro-5(-6)-indenyl acetate, allyl-3-cyclohexyl propionate, allylcyclohexyloxy acetate, benzyl benzoate, benzyl cinnamate, 15-hydroxy-Pentadecanonsaurelacton, 3-methyl-cyclopentadecenone, 1,3,4,6,7,8-hexahydro-4,6,6,7,8,8-hexamethyl cyclopenta[g]-2-benzopyrane, 2-[1-(3,3- dimethylcyclohexyl)ethoxy]-2-methyl-, 1-propanoate, 1,4-dioxacycloheptadecan-5,17-dione, 3-methyl-cyclopentadecanone, 3a,6,6,9a-tetramethyl dodecahydronaphtho[2,1-b]furan, alpha-irone, beta-irone, alpha-n-methylionone, beta-n-methylionone, alpha-isomethylionone, beta-isomethylionone and allyl ionone, 2-methyl-3-(4-tert-butylphenyl)propanal, 4-(4-hydroxy-4-methylpentyl)-3-cyclohexencarboxaldehyde, 2-methyl-4-(2,6,6-trimethyl-1-cyclohexen-1-yl)-2-butenal, 1-methyl-4-(4-methyl-3-penten-1-yl)-3-cyclohexencarboxaldehyde, 3-(3-isopropyl-phenyl)-butyraldehyde, (E)-2,6,10-trimethyl-undeca-5,9-dienal, benzo[1,3]dioxole-5-carbaldehyde, 2,2-dimethyl-3-phenyl-propan-1-ol, 2,2-dimethyl-3-m-tolyl-propan-1-ol, 1-(4-isopropyl-cyclohexyl)-ethanol, (4-isopropyl-cyclohexyl)-methanol, 2-phenyl-ethanol, 2-isobutyl-4-methyl-tetrahydro-pyran-4-ol, 3,7-dimethyl-octa-1,6-dien-3-ol, (Z)-3,7-dimethyl-octa-2,6-dien-1-ol, (E)-3,7-dimethyl-octa-2,6-dien-1-ol, 3,7-dimethyl-oct-6-en-1-ol, 2,6-dimethyl-oct-7-en-2-ol, 3,7-dimethyl-octan-1-ol, 2-methyl-6-methylenoct-7-en-2-ol and (E/Z)-3,7-dimethyl-nona-1,6-dien-3-ol.

9. The fragrance mixture according to claim 6, wherein the proportion of compound(s) of formula (I) in relation to the total weight of the fragrance mixture is 1 wt. % or less.

10. A perfumed product, containing a fragrance mixture according to claim 6, in a sensorially effective quantity,
wherein the proportion of the fragrance ataixture in relation to the total mass of the product is in the range 0.01 through 10 wt %,
wherein the product is selected from the group consisting of perfume extracts, eaux de parfum, eaux de toilettes, aftershaves, eaux de colognes, pre shave products, splash colognes, perfumed freshening wipes, acidic, alkaline and neutral cleaners, textile fresheners, ironing aids liquid laundry detergents, pulverulent laundry detergents, laundry pre-treatment agents, fabric softeners, washing soaps, washing tablets, disinfectants, surface disinfectants, air fresheners, aerosol sprays, waxes and polishes, body care compositions, hand creams and lotions, foot creams and lotions, depilatory creams and lotions after-shave creams and lotions, tanning creams and lotions, hair care products, deodorants and antiperspirants products in decorative cosmetics, candles, lamp oils, joss-sticks, insecticides, repellents and propellants.

11. A method for producing a perfumed product comprising the steps of:
i) providing the ingredients (A) and (B) as defined in claim 6,
ii) providing one or a plurality of further ingredients of the perfumed product, and
iii) bringing, into contact or mixing of the further ingredients provided in step ii) with a sensorially effective quantity of the ingredients (A) and (B) provided in step i).

* * * * *